(12) United States Patent
Oronsky et al.

(10) Patent No.: US 10,543,208 B2
(45) Date of Patent: *Jan. 28, 2020

(54) TREATMENT OF GLIOMAS USING ORGANONITRO COMPOUND COMBINATION THERAPY

(71) Applicant: EpicentRx, Inc., San Diego, CA (US)

(72) Inventors: Bryan T. Oronsky, Los Altos Hills, CA (US); Jan Scicinski, Saratoga, CA (US)

(73) Assignee: EpicentRx, Inc., La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/989,862

(22) Filed: May 25, 2018

(65) Prior Publication Data

US 2019/0125742 A1  May 2, 2019

Related U.S. Application Data

(63) Continuation of application No. 15/337,378, filed on Oct. 28, 2016, now Pat. No. 9,987,270.

(60) Provisional application No. 62/247,846, filed on Oct. 29, 2015.

(51) Int. Cl.
| | | |
|---|---|---|
| *A61K 31/495* | (2006.01) | |
| *A61K 9/00* | (2006.01) | |
| *A61K 31/397* | (2006.01) | |
| *A61K 31/4745* | (2006.01) | |
| *A61N 5/10* | (2006.01) | |

(52) U.S. Cl.
CPC .......... *A61K 31/495* (2013.01); *A61K 9/0019* (2013.01); *A61K 9/0053* (2013.01); *A61K 31/397* (2013.01); *A61K 31/4745* (2013.01); *A61N 5/10* (2013.01)

(58) Field of Classification Search
CPC .. A61K 31/495; A61K 9/0019; A61K 9/0053; A61K 31/397; A61K 31/4745; A61N 5/10; A61N 2005/109; A61N 2005/1087; A61N 2005/1089
USPC ....................................................... 514/800
See application file for complete search history.

(56) References Cited

U.S. PATENT DOCUMENTS

| | | | |
|---|---|---|---|
| 2,978,453 A | 4/1961 | Milton | |
| 3,845,770 A | 11/1974 | Theeuwes et al. | |
| 3,916,899 A | 11/1975 | Theeuwes et al. | |
| 4,584,130 A | 4/1986 | Bucci et al. | |
| 4,765,539 A | 8/1988 | Noakes et al. | |
| 5,112,598 A | 5/1992 | Biesalski | |
| 5,336,784 A | 8/1994 | Hiskey et al. | |
| 5,521,203 A | 5/1996 | Adams et al. | |
| 5,556,611 A | 9/1996 | Biesalski | |
| 5,579,458 A | 11/1996 | Yokosuka et al. | |
| 5,580,988 A | 12/1996 | Dave | |
| 5,679,777 A | 10/1997 | Anderson et al. | |
| 5,693,794 A | 12/1997 | Nielsen | |
| 5,698,155 A | 12/1997 | Grosswald et al. | |
| 5,950,619 A | 9/1999 | van der Linden et al. | |
| 5,954,047 A | 9/1999 | Armer et al. | |
| 5,970,974 A | 10/1999 | Van Der Linden et al. | |
| 6,133,320 A | 10/2000 | Yallampalli et al. | |
| 6,245,799 B1 | 6/2001 | Asselin et al. | |
| 6,391,911 B1 | 5/2002 | Bases | |
| 6,407,236 B1 | 6/2002 | Baraldi et al. | |
| 7,163,958 B2 | 1/2007 | Earl et al. | |
| 7,507,842 B2 | 3/2009 | Oehler et al. | |
| 7,745,643 B2 | 6/2010 | Cannizzo et al. | |
| 8,178,698 B2 | 5/2012 | Cannizzo et al. | |
| 8,299,053 B2 | 10/2012 | Bednarski et al. | |
| 8,664,247 B2 | 3/2014 | Scicinski et al. | |
| 8,927,527 B2 | 1/2015 | Bednarski et al. | |
| 9,139,519 B2 | 9/2015 | Scicinski et al. | |
| 9,226,915 B2 | 1/2016 | Bednarski et al. | |
| 9,468,625 B2 | 10/2016 | Scicinski et al. | |
| 9,987,270 B1 * | 6/2018 | Oronsky .............. | A61K 31/495 |
| 10,149,832 B2 | 12/2018 | Bednarski et al. | |
| 10,342,778 B1 | 7/2019 | Oronsky et al. | |
| 2002/0137770 A1 | 9/2002 | Nara et al. | |
| 2003/0092684 A1 | 5/2003 | Fredeking et al. | |
| 2004/0024057 A1 | 2/2004 | Earl et al. | |
| 2004/0167212 A1 | 8/2004 | Bednarski et al. | |
| 2006/0111272 A1 | 5/2006 | Roberts et al. | |
| 2006/0211639 A1 | 9/2006 | Bratzler et al. | |
| 2007/0135384 A1 | 6/2007 | Bednarski et al. | |
| 2008/0255149 A1 | 10/2008 | Dobler et al. | |
| 2008/0256149 A1 | 10/2008 | Bansal et al. | |
| 2009/0093644 A1 | 4/2009 | Cannizzo et al. | |
| 2009/0163466 A1 | 6/2009 | Bednarski et al. | |
| 2009/0192085 A1 | 7/2009 | Robson et al. | |
| 2010/0247682 A1 | 9/2010 | Gladwin et al. | |
| 2010/0260719 A1 | 10/2010 | Zeldis | |
| 2011/0130572 A1 | 6/2011 | Cannizzo et al. | |
| 2011/0195947 A1 | 8/2011 | Straessler et al. | |
| 2012/0149678 A1 | 6/2012 | Oronsky et al. | |
| 2013/0053418 A1 | 2/2013 | Scicinski et al. | |
| 2013/0123216 A1 | 5/2013 | Bednarski et al. | |
| 2014/0308260 A1 | 10/2014 | Oronsky et al. | |
| 2015/0246020 A1 | 9/2015 | Bednarski et al. | |
| 2016/0081981 A1 | 3/2016 | Scicinski et al. | |
| 2016/0199346 A1 | 7/2016 | Bednarski et al. | |
| 2018/0085346 A1 | 3/2018 | Bednarski et al. | |

FOREIGN PATENT DOCUMENTS

| | | |
|---|---|---|
| DE | 10111049 A1 | 9/2002 |
| EP | 0412211 A1 | 2/1991 |

(Continued)

OTHER PUBLICATIONS

"Dose-Escalation Study of RRx-001 in Combination With Whole Brain Radiation in Subjects With Brain Metastases (Brainstorm)" from Clinicaltrials.gov, 2014.

(Continued)

*Primary Examiner* — Kristin A Vajda
(74) *Attorney, Agent, or Firm* — Goodwin Procter LLP

(57) ABSTRACT

The invention provides therapeutic methods and kits for treating a glioma using a particular dosing regimen of the organonitro compound ABDNAZ, radiation therapy, and one of temozolomide, irinotecan, or bevacizumab.

12 Claims, 8 Drawing Sheets

(56) References Cited

FOREIGN PATENT DOCUMENTS

| WO | WO-95/32715 A1 | 12/1995 |
| --- | --- | --- |
| WO | WO-96/36602 A1 | 11/1996 |
| WO | WO-98/16485 A1 | 4/1998 |
| WO | WO-99/16436 A1 | 4/1999 |
| WO | WO-99/59575 A1 | 11/1999 |
| WO | WO-00/06143 A1 | 2/2000 |
| WO | WO-01/077100 A2 | 10/2001 |
| WO | WO-04/032864 A2 | 4/2004 |
| WO | WO-04/098538 A2 | 11/2004 |
| WO | WO-04/113281 A1 | 12/2004 |
| WO | WO-05/046661 A2 | 5/2005 |
| WO | WO-2007/022121 A2 | 2/2007 |
| WO | WO-2007/022225 A2 | 2/2007 |
| WO | WO-2013/052803 A2 | 4/2013 |
| WO | WO-2017/123593 A1 | 7/2017 |

OTHER PUBLICATIONS

"Phase 1 Two Part Dose Escalation Trial of RRx-001 + Radiation + Temozolomide and RRx-001 + Temozolomide Post-RT in Newly Diagnosed Glioblastoma and Anaplastic Gliomas (G-FORCE-1)" from Clinicaltrials.gov, dated Oct. 24, 2016.

Akhavan, Jacqueline, Explosives and Propellants, Kirk-Othmer Encyclopedia of Chemical Technology, Sep. 17, 2004, pp. 719-744.

Alderman, D., "A Review of Cellulose Ethers in Hydrophilic Matrices for Oral Controlled-Release Dosage Forms," Int. J. Pharm. Tech. & Prod. Mfr., 1984, vol. 5, No. 3, pp. 1-9.

Ansari et al., "Primary squamous cell carcinoma of the prostate: a rare clinicopathological entity. Report of 2 cases and review of literature," Urol. Int., 2001, vol. 66, No. 4, pp. 216-219 (abstract).

Archibald et al., "Synthesis and X-ray Crystal Structure of 1,3,3-Trinitroazetidine," J. Org. Chem., 1990, vol. 55, pp. 2920-2924.

Australian Examination Report No. 2 on patent application No. 2006279589, dated May 18, 2012.

Bamba et al., "Release Mechanisms in Gelforming Sustained Release Preparations," Int. J. Pharm., 1979, vol. 2, pp. 307-315.

Chawla, Garima, et al., "Challenges in Polymorphism of Pharmaceuticals," CRIPS, vol. 5, No. 1, Jan.-Mar. 2004, pp. 9-12.

Coburn et al., caplus an 1998:567551.

Crowder et al., (1999) "Vibrational analysis of high-energy compounds: 1,3,3-trinitroazetidine and 1-acetyl-3, 3-dinitroazetidine," Journal of Energetic Materials, vol. 17(1), pp. 49-68.

Crowder et al., caplus an 1999: 171384.

Dave, P., "Acylative Dealkylation of N-tert-Butyl-3-substituted Azetidines: Facile Access to [1.1.0] Azabicyclobutane, 3-Hydroxyazetidinium Hydrochloride, and 3-Azetidinones," J. Org. Chem., 1996, vol. 61, pp. 5453-5455.

Dave, P.R. et al., "Convenient Acylative Dealkylation of Tertiary Amines," Journal of Organic Chemistry, 2000, vol. 65, pp. 1207-1209.

During et al., "Controlled Release of Dopamine from a Polymeric Brain Implant: In Vivo Characterization," Annals of Neurology, 1989, vol. 25, No. 4, pp. 351-356.

Electrochemical Oxidation of Alkylnitro Compounds PP-1345, A SERDP 'SEED' Activity, initial submission Jun. 30, 2004; amended Aug. 17, 2004; points of contact Scott K. Lusk and Alan N. Green.

Feuer et al., "The Mannich reaction of certain dinitro alcohols with glycine and ethanolamine," Journal of American Chemical Society, 1954, vol. 76, pp. 5124-5126.

Garver et al., "Catalyzed Oxidative Nitration of Nitronate Salts," J. Org. Chem. 1985, vol. 50, No. 10, pp. 1699-1702.

Goodson, J. Max, "Dental Applications," Chapter 6 of Medical Applications of Controlled Release, vol. II, pp. 115-138, CRC Press, Inc., Boca Raton, FL, copyright 1984.

Granelli, P. "SEL 1L and Squamous Cell Carcinoma of the Esophagus," Clinical Cancer Research, 2004, vol. 10, pp. 5857-5861.

Hiskey et al., "Preparation of 1-Substituted-3,3-Dinitroazetidines," Journal of Energetic Materials, 1999, vol. 17, pp. 233-254.

Hiskey et al., caplus an 1993:233785.

Hiskey et al., caplus an 1994:700750.

Hiskey et al., caplus an 1999:411860.

Hockel et al., "Tumor Hypoxia: Definitions and Current Clinical, Biologic, and Molecular Aspects," Journal of the National Cancer Institute, 2001, vol. 93, No. 4, pp. 266-276.

Howard et al., "Intracerebral Drug Delivery in Rats with Lesion-Induced Memory Deficits," J. Neurosurg., 1989, vol. 71, pp. 105-112.

Huguenin, Sandra, et al., "Evaluation of the antitumoral potential of different nitric oxide-donating non-steroidal anti-inflammatory drugs (NO-NSAIDs) on human urological tumor cell lines," Cancer Letters (2005) vol. 218, pp. 163-170.

International Search Report and Written Opinion for PCT/US2011/064178 dated Apr. 17, 2012. (8 pages).

International Search Report and Written Opinion for PCT/US2012/038592 dated Aug. 10, 2012. (11 pages).

International Search Report for PCT/US2006/031722 dated May 29, 2007.

International Search Report for PCT/US2006/031917 dated Jul. 20, 2007.

International Search Report for PCT/US2011/021500 dated May 3, 2011.

Jia, Q., et al. "NO donors with anticancer activity," Expert Opin. Therapeut. Patents (2002) vol. 12, No. 6, pp. 819-826.

Johnson, J.. et al., "Relationships Between Drug Activity in NCI Preclinical in Vitro and in Vivo Models and Early Clinical Trials," British J. Cancer (2001) vol. 84, No. 10, pp. 1424-1431.

Kashfi, Khosrow, et al., "Nitric Oxide-Donating Nonsteroidal Anti-Inflammatory Drugs Inhibit the Growth of Various Cultured Human Cancel Cells: Evidence of a Tissue Type-Independent Effect," J. Pharmacology Experimental Therapeutics (2002) vol. 303, No. 3, pp. 1273-1282.

Katritzky et al., "Novel Syntheses of 1,3,3-Trinitroazetidine," J. Heterocyclic Chem., Mar.-Apr. 1994, vol. 31, pp. 271-275.

Konovalova, N.P., et al., "Nitric oxide donor increases the efficiency of cytostatic therapy and retards the development of drug resistance," Nitric Oxide (2003) vol. 8, No. 1, pp. 59-64.

Kornblum et al., "Oxidative Substitution of Nitroparaffin Salts," J. Org. Chem., 1983, vol. 48, pp. 332-337.

Langer et al., "Chemical and Physical Structure of Polymers as Carriers for Controlled Release of Bioactive Agents: A Review, " JMS-Rev. Macromol. Chem. Phys., 1983, Ch. 23, pp. 61-126.

Langer, R., "New Methods of Drug Delivery," Science (1990) vol. 249, No. 4976, pp. 1527-1533.

Langer, Robert S., et al., eds., "Medical Applications of Controlled Release," vol. 1, Classes of Systems, Ch. 2, pp. 42-67, CRC Press, Inc., Boca Raton, FL, copyright 1984.

Levy, R., et al. "Inhibition of Calcification of Bioprosthetic Heart Valves by Local Controlled-Release Diphosphonate," Science (1985) vol. 228, No. 4696, pp. 190-192.

Ling et al., "Phase I study of Cm—Na combined with concurrent radiochemotherapy for advanced esophageal carcinoma," Chinese Journal of Cancer, 2005, vol. 24, No. 5, (abstract).

Lopez-Ferrer et al., "Differences in the O-Glycosylation Patterns Between Lung Squamous Cell Carcinoma and Adenocarcinoma," Am. J. Clin. Pathol., 2002, vol. 118, pp. 749-755.

Marchand et al., "A Novel Approach to the Synthesis of 1,3,3-Trinitroazetidine," J. Org Chem. 1995, vol. 60, No. 15, pp. 4943-4946.

Marchand, A. P. et al., "Additions of X-Y Across the C(3)-N σ-Bond in 1-Aza-3-ethylbicyclo[1.1.0]butane, Novel Routes to 3-Substituted Azetidines," Journal of Organic Chemistry, 1994, vol. 59, No. 18, pp. 5499-5501.

Maxwell et al., "Hypoxia-inducible factor-1 modulates gene expression in solid tumors and influences both angiogenesis and tumor growth," Proc. Natl. Acad. Sci. USA, 1997, vol. 94, pp. 8104-8109.

McKenney et al., "Synthesis and thermal properties of 1,3-dinitro-3-(1', 3'-dinitroazetidin-3'-yl) azetidine (TNDAZ) and its admixtures with 1,3,3-trinitroazetidine (TNAZ)," Journal of Energetic Materials, 1998, vol. 16, pp. 199-235.

(56) References Cited

OTHER PUBLICATIONS

Mendenhall, William M., et al., "Radiation Therapy for Squamous Cell Carcinoma of the Tonsillar Region: A Preferred Alternative to Surgery?" *J. Clinical Oncology* (2000) vol. 18, No. 11, pp. 2219-2225.
Morales-Suarez-Varela, Maria M., et al., "Impact of Nitrates in Drinking Water on Cancer Mortality in Valencia, Spain," European Journal of Epidemiology, 1995, pp. 15-21, vol. 11.
Muehlstaedt et al., CAPLUS, 1976:89768, Copyright 2008. (1 page).
Naimi, Ebrahim, et al., "Synthesis of 3'- and 5'-Nitrooxy Pyrimidine Nucleoside Nitrate Esters: "Nitric Oxide Donor" Agents for Evaluation as Anticancer and Antiviral Agents," *J. Med. Chem.* (2003) vol. 46, pp. 995-1004.
Nara et al., caplus an 2002:169585; 2002.
Newman, Ann W. and Byrn, Stephen R. "Solid-state analysis of the active pharmaceutical ingredient in drug products," *Drug Discovery Today* (2003) vol. 8, No. 19, pp. 898-905.
Ning, S. et al., "Dinitroazetidines Are a Novel class of Anticancer Agents and Hypoxia-Activated Radiation Sensitizers Developed from Highly Energetic Materials," *Cancer Res.* (2012) vol. 72, pp. 2600-2608.
Nitrates and Nitrites Answers to Frequently Asked Questions, Ohio Bureau of Environmental Health, Health Assessment Section, Nov. 1, 2006. (2 pages).
Oronsky, B. T. et al., "A Review of Two Promising Radiosensitizers in Brain Metastases: Rrx-001 and 2-Deoxyglucose," *J. Cancer Sci. Ther.* (2015) vol. 7, pp. 137-141.
Oxley J. et al., "Thermal Decomposition Pathways of 1,3,3-Trinitroazetidine (TNAZ), Related 3,3-Dinitroazetidium Salts, and 15N, 13C, and 2H Isotopomers," *Journal of Physical Chemistry A*, 1997, vol. 101, No. 24, pp. 4375-4383.
Padwa et al., "Diastereofacial selectivity in azomethine ylide cycloaddition reactions derived from chiral o-cyanoaminosilanes," *Tetrahedron* (1985) vol. 41, No. 17, pp. 3529-3535.
Peiris, S. M. et al., "Structures of dinitroazetidine and three of its carbonyl derivatives," *Journal of Chemical Crystallography*, 2001, vol. 30, No. 10, pp. 647-653.
Prezioso, J.A., et al., Genetic Toxicity Evaluation of 1, 3, 3-Trinitroazetidine, vol. IV: Summary Report on the Genotoxicity of TNAZ, AL/OE-TR-1994-0069 vol. IV of IV, Oct. 1994, 22 pages, Air Force Materiel Command, Wright-Patterson Air Force Base, Ohio.
Raleigh et al. "Pharmacokinetics of Isotretinoin (ISO) in Rats Following Oral Dosing or Aerosol Inhalation," *British J. Cancer*, 1999, vol. 80, Suppl. 2, 96, p. 269.
Remington, "The Science and Practice of Pharmacy," 19th Edition, vol. II, pp. 1495-1562, 1577-1614, and 1660-1692; Mack Publishing Company, Easton, PA, 1995.
Rosenthal, David I., "A Phase I Single-Dose Trial of Gadolinium Texaphyrin (Gd-Tex), a Tumor Selective Radiation Sensitizer Detectable by Magnetic Resonance Imaging," *Clinical Cancer Research* (1999) vol. 5, No. 4, pp. 739-745.
Sandler, G., "Clinical evaluation of propatylnitrate in angina pectoris," *British Medical Journal*, vol. 2, No. 5269 (Dec. 30, 1961), pp. 1741-1744.
Sauder, C. "A Preliminary Trial of the Programmable Implantable Medication System for Insulin Delivery", *The New England Journal of Medicine*, 1989, vol. 321, No. 9, pp. 574-579.
Sausville, Edward A., et al., "Contributions of Human Tumor Xenografts to Anticancer Development," *Cancer Research* (2006) vol. 66, No. 7, pp. 3351-3354.
Sefton, M., "Implantable Pumps," *CRC Crit. Rev. Biomed. Eng.*, 1987, vol. 14, No. 3, pp. 201-237.
Shokeir, A., "Squamous Cell Carcinoma of the Bladder: pathology, diagnosis and treatment," *BJU International*, 2004, vol. 93, pp. 216-220.
Sikder et al., "1,3,3-Trinitroazetidine (TNAZ), a melt-cast explosive: synthesis, characterization and thermal behavior," *Journal of Hazardous Materials*, vol. 113, 2004, pp. 35-43.
Simpson, R.L., et al., Characterization of TNAZ, UCRL-ID-119672, Dec. 14, 1994, Lawrence Livermore National Laboratory, 15 pages.
Smolen, Victor F., et al., eds., "Controlled Drug Bioavailability," vol. 1, Drug Product Design and Performance, Ch. 7, pp. 203-237, John Wiley & Sons, New York, NY, copyright 1984.
Stamler, J.S., et al., "Inhaled ethyl nitrite gas for persistent pulmonary hypertension in infants," *The Lancet* (2002) vol. 360, No. 9350, p. 2077.
Straessler et al., "Development of a Safe and Efficient Two-Step Synthesis for Preparing 1-Bromoacetyl-3,3-dinitroazetidine, a Novel Clinical Anticancer Candidate," *Organic Process Research & Development*, 2012, vol. 16, pp. 512-517.
Stratford et al., "Bioreductive drugs into the next millennium," *Anti-Cancer Drug Design*, 1998, vol. 13, pp. 519-528.
TEMODAR Prescribing Information (year 2008).
Treat, Joseph, et al., "Liposome Encapsulated Doxorubicin: Preliminary Results of Phase I and Phase II Trials," pp. 353-365 of "Liposomes in the Therapy of Infectious Diseases and Cancer, Proceedings of the Ciba-Geigy-Squibb-UCLA Colloquium at Lake Tahoe, CA, Feb. 16-20, 1988," Lopez-Berestein, G. and Fidler, I. J. (eds.), Alan R. Liss, Inc., New York, 1989.
Verma et al., "Osmotically Controlled Oral Drug Delivery," *Drug Dev. Ind. Pharm.*, 2000, vol. 26, No. 7, pp. 695-708.
Watt, Duncan S. and Cliff, Matthew D. "Evaluation of 1,3,3-Trinitrozaetidine (TNAZ)—A High Performance Melt-Castable Explosive," Weapons Systems Division, Aeronautical and Maritime Research Laboratory, Melbourne, Australia. Report No. DSTO-TR-1000, Issue date Jul. 2000. (34 pages).
Watt, Duncan S. and Cliff, Matthew D. "TNAZ Based Melt-Cast Explosives: Technology Review and AMRL Research Directions," Weapons Systems Division, Aeronautical and Maritime Research Laboratory, Melbourne, Australia. Report DSTO-TR-0702, Issue date Jul. 1998. (37 pages).
West, Anthony R., Solid State Chemistry and its Applications, 1988, pp. 358, and 365, Wiley, New York.
Wilson, et al., "Radiation-activated prodrugs as hypoxia-selective cytotoxins: model studies with nitroarylmethyl quaternary salts," *Anti-Cancer Drug Design*, 1998, vol. 13, pp. 663-685.
Written Opinion of the International Searching Authority for PCT/US2006/031722 dated May 29, 2007.
Written Opinion of the International Searching Authority for PCT/US2006/031917 dated Jul. 20, 2007.
Written Opinion of the International Searching Authority for PCT/US2011/021500 dated May 2011.
Yarmukhamedov et al., "One-step synthesis of substituted 3,5-dinitropiperidines and 1,5-dinitro-3,7-diazabicyclo(3.3.1)nonanes from 1,3-dinitropropanes," *Russian Chemical Bulletin, International Edition*, 2005, vol. 54, No. 2, pp. 414-420.
Yen et al., "$^{18}$F-FDG Uptake in Squamous Cell Carcinoma of the Cervix is Correlated with Glucose Transporter 1 Expression," *The Journal of Nuclear Medicine*, 2004, vol. 45, No. 1, pp. 22-29.
Zhang et al, caplus an 1998:460439.
Dave, 1997, caplus an 1997: 67373.
Li et al., 2006, caplus an 2006:150006.
Gladwin et al., "The Emerging Biology of the Nitrite Anion," in Nature Chemistry and Biology, 2005, vol. 1, pp. 308-314, p. 308, col. 1, para 1; p. 308, col. 2, para 2; p. 310, col. 2, para. 3-4; p. 309, figure1; p. 310, figure 2; p. 311, figure 3.
S.S. Wong in *Chemistry of Protein Conjugation and Cross-linking*; CRC Press: Boca Raton, 1991, p. 147.
Wu et al. In *AAPS PharmSciTech* (2011) vol. 12, pp. 1248-1263.
International Search Report and Written Opinion for PCT/US12/58964, dated Apr. 5, 2013, 9 pages.
Weyerbrock et al., Journal of Neurosurgery, 2003, 99(4), 728-737.
Schwartz, R., Am. J. Health-Syst. Pharm., 2007, 64 (Supplement 2), S5-S13.
Heller, ECS Transactions, 2010, 28(33), 1-6.
Vascular Tumor, 2018, <https://www.cancer.gov/publications/dictionaries/cancer-terms/def/vascular-tumor>.
International Search Report and Written Opinion for PCT/US2017/012948 dated Mar. 28, 2017 (8 pages).

(56) References Cited

OTHER PUBLICATIONS

Fitch et al, Abstract WRM 267, "High resolution MS proves that the developmental cancer drug, RRx-001, alkylates the hemoglobin beta chain", 44th Western Regional Meeting of the American Chemical Society, Oct. 3-6, 2013, Available from the Internet, <URL: http://acswrm.org/wrm2013/files/Abstracts_SaturdayAM.pdf>, Last Retrieved Mar. 21, 2017.

Oronsky et al, "RRx-001: a systemically non-toxic M2-to-M1 macrophage stimulating and prosensitizing agent in Phase II clinical trials", Expert Opinion on Investigational Drugs (2017), vol. 26, No. 1, pp. 109-119, Published Dec. 21, 2016.

NCT02489903, Jul. 2, 2015, "An Open-label, Three Stage, Three Arm Pilot Study of RRx-001 for Second Line or Greater Small Cell Lung Cancer, Third Line or Greater Non-Small Lung Cancer, and Second Line or Greater High Grade Neuroendocrine Tumors Prior to Re-administration of Platinum Based Doublet Regimens (Triple Threat)", Available from the Internet, <URL: https://clinicaltrials.gov/archive/NCT02489903/2015_07_02>.

Scicinski et al, "Preclinical Evaluation of the Metabolism and Disposition of RRx-001, a Novel Investigative Anticancer Agent", Drug Metabolism and Disposition (2012), vol. 40, No. 9, pp. 1810-1816.

Cabrales et al, "A look inside the mechanistic black box: Are red blood cells the critical effectors of RRx-001 cytotoxicity?", Medical Oncology (2016), vol. 33, No. 7, Article No. 63, 7 pages, doi:10.1007/s12032-016-0775-3.

* cited by examiner

TREATMENT OF GLIOMAS USING ORGANONITRO COMPOUND COMBINATION THERAPY

CROSS REFERENCE TO RELATED APPLICATION

This application is a continuation patent application under 35 U.S.C. § 120 of U.S. patent application Ser. No. 15/337,378, filed on Oct. 28, 2016, which claims the benefit of and priority to U.S. Provisional Patent Application No. 62/247,846, filed on Oct. 29, 2015, the contents of each of which are hereby incorporated by reference herein, in their entirety.

FIELD OF THE INVENTION

The invention provides therapeutic methods and kits for treating a glioma using a particular dosing regimen of the organonitro compound ABDNAZ, radiation therapy, and one of temozolomide, irinotecan, or bevacizumab.

BACKGROUND

Gliomas are tumors that arise from glial tissue of the brain. Gliomas are often found in the cerebral hemispheres of the brain, but can be found anywhere in the brain. Because gliomas can grow rapidly, common symptoms experienced by patients suffering from a glioma are often associated with an increased pressure in the brain. The symptoms can include headache, nausea, vomiting, and drowsiness. In addition, patients suffering from a glioma may develop other symptoms such as weakness on one side of the body, memory and/or speech difficulties, and visual changes, often as function of the location of the glioma tumor.

Gliomas can be characterized according to grade, where low-grade gliomas [WHO grade II] are typically well-differentiated and tend to exhibit benign tendencies. Low-grade gliomas stand in contrast to high-grade gliomas [WHO grade III or IV] that are typically undifferentiated and frequently malignant. One example of a high-grade glioma is glioblastoma multiforme. Glioblastoma multiforme has been characterized as a World Health Organization grade IV astrocytoma, with an incidence in North America of 5.0 per 100,000 in the population, representing 15 to 20% of all primary intracranial neoplasms.

Currently available therapeutic approaches for treating patients suffering from a glioma include surgery, radiation therapy, and treatment with certain anti-cancer agents. A typical first step in treating a glioblastoma is to surgically remove as much tumor as possible. This can help alleviate pressure on the brain. However, glioblastomas often have finger-like tentacles, and as a result it can be difficult to completely remove all the glioblastoma. This is particularly true when a glioblastoma appears near parts of the brain that control important functions, such as language and coordination. Radiation and chemotherapy may be used to help slow the growth of glioblastoma tumors that cannot be removed with surgery. However, survival rates are low using current standard treatments for glioblastoma. For example, using standard treatments currently approved by government regulatory agencies, the median survival time for adults with an anaplastic astrocytoma has been reported to be about two to three years. For children suffering from a high-grade glioma tumor (grade III or IV), the five-year survival rate has been reported to be about twenty-five percent.

As a result, there is a need for additional therapies to treat patients suffering from a glioma. The present invention addresses this need and provides other related advantages.

SUMMARY

The invention provides therapeutic methods and kits for treating a glioma using a particular dosing regimen of the organonitro compound ABDNAZ, radiation therapy, and one of temozolomide, irinotecan, or bevacizumab. The compound ABDNAZ has the following chemical structure:

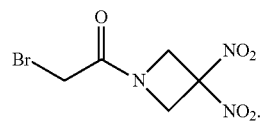

The therapeutic methods and kits provide a solution to the long unmet need for a more effective treatment for patients suffering from a glioma. The therapeutic method generally entails (a) administering to the patient in need thereof a therapeutically effective amount of a formulation comprising temozolomide, irinotecan, or bevacizumab, and within a certain amount of time (e.g., about 7 days) subjecting the glioma to radiation therapy, and (b) administering to the patient at least one dose of a therapeutically effective amount of a formulation comprising ABDNAZ within about 7 days of administration of a first dose of the temozolomide, irinotecan, or bevacizumab, in order to treat the glioma. In preferred embodiments, the radiation therapy may be administered to the patient for a select number of days (e.g., at least 2, 3, 4, or 5 days) over a two-week period, or longer duration of time depending on patient response to the therapy. In preferred embodiments, the formulation comprising ABDNAZ may be administered to the patient for a select number of days per week (e.g., at least 2, 3, or 4 days per week) over a two-week period, or longer duration of time depending on patient response to the therapy. The therapy may be used to treat various types of gliomas, such as, for example, a primary glioblastoma or a secondary glioblastoma. The invention having been generally described is explained in more detail in the aspects and embodiments below and in the detailed description.

Accordingly, one aspect of the invention provides a method of treating a glioma in a patient. The method comprises the steps of: (a) administering to the patient in need thereof a therapeutically effective amount of a formulation comprising temozolomide, and within about 2 days thereafter subjecting the glioma to radiation therapy; and (b) administering to the patient at least one dose of a therapeutically effective amount of a formulation comprising ABDNAZ within about 7 days of administration of a first dose of the temozolomide; to treat the glioma.

Another aspect of the invention provides a method of treating a glioma in a patient. The method comprises the steps of: (a) administering to the patient in need thereof a therapeutically effective amount of a formulation comprising irinotecan, and within about 7 days subjecting the glioma to radiation therapy; and (b) administering to the patient at least one dose of a therapeutically effective amount of a formulation comprising ABDNAZ within about 7 days of administration of a first dose of the irinotecan; to treat the glioma.

Another aspect of the invention provides a method of treating a glioma in a patient. The method comprises the steps of: (a) administering to the patient in need thereof a therapeutically effective amount of a formulation comprising bevacizumab, and within about 7 days subjecting the glioma to radiation therapy; and (b) administering to the patient at least one dose of a therapeutically effective amount of a formulation comprising ABDNAZ within about 7 days of administration of a first dose of the bevacizumab; to treat the glioma.

Another aspect of the invention provides a kit for treating a glioma. In certain embodiments, the kit comprises: (i) a formulation comprising ABDNAZ, and (ii) instructions for treating a glioma according to procedures described herein, such as (a) administering to the patient in need thereof a therapeutically effective amount of a formulation comprising temozolomide, and within about 2 days thereafter subjecting the glioma to radiation therapy; and (b) administering to the patient at least one dose of a therapeutically effective amount of a formulation comprising ABDNAZ within about 7 days of administration of a first dose of the temozolomide; to treat the glioma. In an alternative embodiment, the kit comprises: (i) a formulation comprising ABDNAZ, and (ii) instructions for treating a glioma that comprise (a) administering to the patient in need thereof a therapeutically effective amount of a formulation comprising irinotecan, and within about 7 days subjecting the glioma to radiation therapy; and (b) administering to the patient at least one dose of a therapeutically effective amount of a formulation comprising ABDNAZ within about 7 days of administration of a first dose of the irinotecan; to treat the glioma.

DETAILED DESCRIPTION

Figure 1:
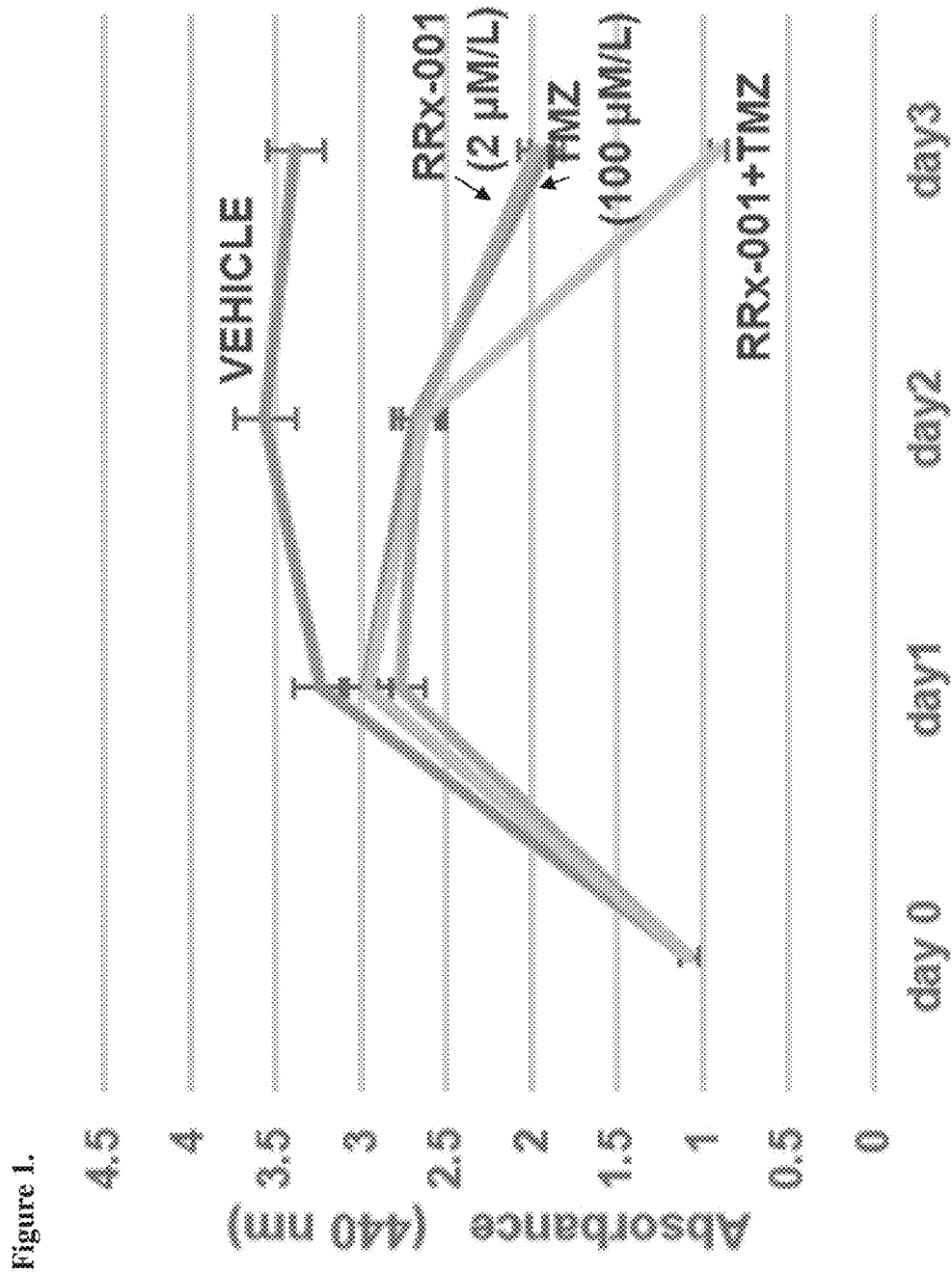
FIG. 1 is a graph showing response observed using a GBM14 TMZ-S patient-derived cell line, as described in Example 3.

The invention provides therapeutic methods and kits for treating a glioma using a particular dosing regimen of the organonitro compound ABDNAZ, radiation therapy, and one of temozolomide, irinotecan, or bevacizumab. The compound ABDNAZ has the following chemical structure:

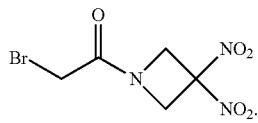

The therapeutic methods and kits provide a solution to the long unmet need for a more effective treatment for patients suffering from a glioma. The therapeutic method generally entails (a) administering to the patient in need thereof a therapeutically effective amount of a formulation comprising temozolomide, irinotecan, or bevacizumab, and within a certain amount of time (e.g., about 7 days) subjecting the glioma to radiation therapy, and (b) administering to the patient at least one dose of a therapeutically effective amount of a formulation comprising ABDNAZ within about 7 days of administration of a first dose of the temozolomide, irinotecan, or bevacizumab, in order to treat the glioma. In preferred embodiments, the radiation therapy may be administered to the patient for a select number of days (e.g., at least 2, 3, 4, or 5 days) over a two-week period, or longer duration of time depending on patient response to the therapy. In preferred embodiments, the formulation comprising ABDNAZ may be administered to the patient for a select number of days per week (e.g., at least 2, 3, or 4 days per week) over a two-week period, or longer duration of time depending on patient response to the therapy. The therapy may be used to treat various types of gliomas, such as, for example, a primary glioblastoma or a secondary glioblastoma.

Various aspects of the invention are set forth below in sections; however, aspects of the invention described in one particular section are not to be limited to any particular section.

I. Therapeutic Methods for Treating a Glioma

The invention provides therapeutic methods for treating a glioma using a particular dosing regimen of the organonitro compound ABDNAZ, radiation therapy, and one of temozolomide, irinotecan, or bevacizumab. The therapeutic methods provide a solution to the long unmet need for a more effective treatment for patients suffering from a glioma. The therapeutic method generally entails (a) administering to the patient in need thereof a therapeutically effective amount of a formulation comprising temozolomide, irinotecan, or bevacizumab, and within a certain amount of time (e.g., about 7 days) subjecting the glioma to radiation therapy, and (b) administering to the patient at least one dose of a therapeutically effective amount of a formulation comprising ABDNAZ within about 7 days of administration of a first dose of the temozolomide, irinotecan, or bevacizumab, in order to treat the glioma.

The invention also provides methods for increasing the amount of temozolomide, irinotecan, or bevacizumab in a glioma. The method generally involves administering to a patient having a glioma (i) a first formulation comprising temozolomide, irinotecan, or bevacizumab and (ii) an effective amount of a formulation comprising ABDNAZ so that the ABDNAZ exerts physiological activity during a time period in which the temozolomide, irinotecan, or bevacizumab is present in the patient, in order to increase the amount of the temozolomide, irinotecan, or bevacizumab in the glioma.

Various features of the methods are described in sections below. The sections are arranged for convenience and information in one section is not limited to that section, but may be applied to other sections.

First Method—Using Temozolomide

One aspect of the invention provides a method of treating a glioma in a patient. The method comprises the steps of: (a) administering to the patient in need thereof a therapeutically effective amount of a formulation comprising temozolomide, and within about 2 days thereafter subjecting the glioma to radiation therapy; and (b) administering to the patient at least one dose of a therapeutically effective amount of a formulation comprising ABDNAZ within about 7 days of administration of a first dose of the temozolomide; to treat the glioma.

Temozolomide is a small molecule having the chemical name 3,4-dihydro-3-methyl-4-oxoimidazo[5,1-d]-as-tetrazine-8-carboxamide, which is marketed commercially under the tradename TEMODAR®.

Exemplary Features of the Method

The above method may be further characterized by additional features, such as the dosing schedule and amount of temozolomide, dosing schedule of ABDNAZ, dosing amount for ABDNAZ, features of the radiation therapy, and the rest period/maintenance period.

Dosing Schedule and Amount of Temozolomide

The method can be further characterized according to the dosing schedule and amount of the temozolomide. Accordingly, in certain embodiments, the formulation comprising temozolomide is administered daily for at least 2 weeks. In certain embodiments, the formulation comprising temozolomide is administered daily for at least 4 weeks. In certain embodiments, the formulation comprising temozolomide is administered daily for at least 6 weeks. In certain embodiments, the formulation comprising temozolomide is administered at the patient's bedtime.

In certain embodiments, the patient receives temozolomide by oral administration at a daily dose of at least 50 $mg/m^2$. In certain embodiments, the patient receives temozolomide by oral administration at a daily dose of about 50 $mg/m^2$ to about 100 $mg/m^2$. In certain embodiments, the patient receives temozolomide by oral administration at a daily dose of about 75 $mg/m^2$.

Dosing Schedule of ABDNAZ

A formulation comprising ABDNAZ may be administered multiple times, such as multiple times over a defined period of time. Further, coordination of the dosing schedule of the temozolomide and radiation therapy with that of the formulation comprising ABDNAZ is contemplated to provide therapeutic benefits, such as superior efficacy.

In certain embodiments, for a duration of at least 2 weeks following administration of the first dose of temozolomide, the patient receives at least one dose each week of a therapeutically effective amount of a formulation comprising ABDNAZ. In certain embodiments, for a duration of at least 4 weeks following administration of the first dose of temozolomide, the patient receives at least one dose each week of a therapeutically effective amount of a formulation comprising ABDNAZ. In certain embodiments, for a duration of at least 6 weeks following administration of the first dose of temozolomide, the patient receives at least one dose each week of a therapeutically effective amount of a formulation comprising ABDNAZ. In certain embodiments, two doses of a therapeutically effective amount of a formulation comprising ABDNAZ are administered within about 7 days of administration of the first dose of temozolomide. In certain embodiments, for a duration of at least 2 weeks following administration of the first dose of temozolomide, the patient receives two doses each week of a therapeutically effective amount of a formulation comprising ABDNAZ. In certain embodiments, for a duration of at least 4 weeks following administration of the first dose of temozolomide, the patient receives two doses each week of a therapeutically effective amount of a formulation comprising ABDNAZ. In certain embodiments, for a duration of at least 6 weeks following administration of the first dose of temozolomide, the patient receives two doses each week of a therapeutically effective amount of a formulation comprising ABDNAZ.

In certain embodiments, for a duration of at least 2 weeks following administration of the first dose of temozolomide, the patient receives one dose each week of a therapeutically effective amount of a formulation comprising ABDNAZ. In certain embodiments, for a duration of at least 4 weeks following administration of the first dose of temozolomide, the patient receives one dose each week of a therapeutically effective amount of a formulation comprising ABDNAZ. In certain embodiments, for a duration of at least 6 weeks following administration of the first dose of temozolomide, the patient receives one dose each week of a therapeutically effective amount of a formulation comprising ABDNAZ. In certain embodiments, for a duration of 6 weeks following administration of the first dose of temozolomide, the patient receives one dose each week of a therapeutically effective amount of a formulation comprising ABDNAZ.

In certain embodiments, any dose of ABDNAZ administered to the patient within 12 hours of administering temozolomide is administered at least 3 hours before administering the temozolomide.

In certain embodiments, the patient receives ABDNAZ within about 3 hours prior to subjecting the glioma to radiation therapy. In certain embodiments, the patient receives ABDNAZ within about 6 hours prior to subjecting the glioma to radiation therapy. In certain embodiments, the patient receives ABDNAZ within about 24 hours prior to subjecting the glioma to radiation therapy. In certain embodiments, the patient receives ABDNAZ within about 48 hours prior to subjecting the glioma to radiation therapy.

In certain embodiments, the formulation comprising ABDNAZ is administered so that the ABDNAZ exerts physiological activity during an overlapping time period with one or both of the radiation therapy and temozolomide.

Dosing Amount of ABDNAZ

The method may be further a characterized according to the dose of ABDNAZ administered to the patient. The dose of ABDNAZ described herein for use in combination with temozolomide and the radiation therapy has been selected in view of the dosing schedule and amount of temozolomide and the radiation therapy. Dosing amounts of ABDNAZ are provided according to the number of milligrams of ABDNAZ to be administered to the patient based on the surface area of the patient as measured in $m^2$.

In certain embodiments, each dose of the formulation comprising ABDNAZ is administered to the patient by intravenous infusion. In certain embodiments, each dose of the formulation comprising ABDNAZ is administered to the patient by intravenous infusion providing ABDNAZ in an amount ranging from about 2 $mg/m^2$ to about 20 $mg/m^2$. In certain embodiments, each dose of the formulation comprising ABDNAZ is administered to the patient by intravenous infusion providing ABDNAZ in an amount ranging from about 2.5 $mg/m^2$ to about 5 $mg/m^2$. In certain embodiments, each dose of the formulation comprising ABDNAZ is administered to the patient by intravenous infusion providing ABDNAZ in an amount ranging from about 5 mg/m$^2$ to about 10 mg/m$^2$. In certain embodiments, each dose of the formulation comprising ABDNAZ is administered to the patient by intravenous infusion providing ABDNAZ in an amount ranging from about 10 mg/m$^2$ to about 16.5 mg/m$^2$. In certain embodiments, each dose of the formulation comprising ABDNAZ is administered to the patient by intravenous infusion providing ABDNAZ in an amount of about 2.5 mg/m$^2$. In certain embodiments, each dose of the formulation comprising ABDNAZ is administered to the patient by intravenous infusion providing ABDNAZ in an amount of about 5 mg/m$^2$. In certain embodiments, each dose of the formulation comprising ABDNAZ is administered to the patient by intravenous infusion providing ABDNAZ in an amount of about 10 mg/m$^2$. In certain embodiments, each dose of the formulation comprising ABDNAZ is administered to the patient by intravenous infusion providing ABDNAZ in an amount of about 16.5 mg/m$^2$.

In certain embodiments, each dose of the formulation comprising ABDNAZ is administered to the patient by intravenous infusion providing ABDNAZ in an amount of from about 0.1 mg to about 20 mg. In certain embodiments, each dose of the formulation comprising ABDNAZ is administered to the patient by intravenous infusion providing ABDNAZ in an amount of from about 0.1 mg to about 10 mg. In certain embodiments, each dose of the formulation comprising ABDNAZ is administered to the patient by intravenous infusion providing ABDNAZ in an amount of from about 0.5 mg to about 4.0 mg. In certain embodiments, each dose of the formulation comprising ABDNAZ is administered to the patient by intravenous infusion providing ABDNAZ in an amount of about 0.5 mg, 1.0 mg, 1.5 mg, 2.0 mg, 2.5 mg, 3.0 mg, 3.5 mg, or 4.0 mg.

Radiation Therapy Features

The method can be further characterized according to the dosing schedule and amount of radiation administered for the radiation therapy.

In certain embodiments, the glioma is subjected to radiation therapy once per day for at least 3 days within a 7 day period following administration of the first dose of temozolomide. In certain embodiments, the glioma is subjected to radiation therapy once per day for at least 5 days within a 7 day period following administration of the first dose of temozolomide. In certain embodiments, for a duration of at least 2 weeks following administration of the first dose of temozolomide, the glioma is subjected to radiation therapy once per day for at least 3 days of each week. In certain embodiments, for a duration of at least 4 weeks following administration of the first dose of temozolomide, the glioma is subjected to radiation therapy once per day for at least 3 days of each week. In certain embodiments, for a duration of at least 6 weeks following administration of the first dose of temozolomide, the glioma is subjected to radiation therapy once per day for at least 3 days of each week. In certain embodiments, for a duration of at least 2 weeks following administration of the first dose of temozolomide, the glioma is subjected to radiation therapy once per day for at least 5 days of each week. In certain embodiments, for a duration of at least 4 weeks following administration of the first dose of temozolomide, the glioma is subjected to radiation therapy once per day for at least 5 days of each week. In certain embodiments, for a duration of at least 6 weeks following administration of the first dose of temozolomide, the glioma is subjected to radiation therapy once per day for at least 5 days of each week. In certain embodiments, for a duration of at least 6 weeks following administration of the first dose of temozolomide, the glioma is subjected to radiation therapy once per day for 5 days each week. In certain embodiments, for a duration of 6 weeks following administration of the first dose of temozolomide, the glioma is subjected to radiation therapy once per day for 5 days each week.

In certain embodiments, when radiation therapy is administered to the glioma, the amount of radiation provided to the glioma on the day of administering the radiation therapy is from about 1 Gy to about 3 Gy. In certain embodiments, when radiation therapy is administered to the glioma, the amount of radiation provided to the glioma on the day of administering the radiation therapy is about 2 Gy. In certain embodiments, the glioma is exposed to from about 50 Gy to about 70 Gy of radiation by the radiation therapy over a period of 6 weeks following administration of the first dose of temozolomide. In certain embodiments, the glioma is exposed to about 60 Gy of radiation by the radiation therapy over a period of 6 weeks following administration of the first dose of temozolomide.

In certain embodiments, the radiation therapy is (i) conventional fractionated external beam radiation or (ii) intensity-modulated radiation therapy. In certain embodiments, the radiation therapy is conventional fractionated external beam radiation.

Various types of radiation therapy are used by those skilled in the art and have been described in the literature. Exemplary types of radiation therapy include, for example, radiation therapy comprising gamma rays, X-rays, electron beams, neutron beams, particulate radiation, proton beams, or the like. The source of the radiation is desirably external to the patient, which involves directing a beam of high-energy radiation to the glioma using a machine external to the patient. Desirably the target site (i.e., site of the glioma) is exposed to the radiation therapy for a short duration of time, such as less than about 3 hours, 2 hours, 1 hour, 30 minutes, 15 minutes, 10 minutes, 5 minutes, or 1 minute for each dose of radiation therapy.

Rest Period/Maintenance Period

The method may be further characterized according to the scope of the rest period/maintenance period. For example, in certain embodiments, after receiving temozolomide for a duration of 6 weeks, the patient does not receive any of temozolomide, radiation therapy, or ABDNAZ for a duration of at least about 2 weeks.

In certain embodiments, the patient after having not received any of temozolomide, radiation therapy, or ABDNAZ for a duration of at least about 2 weeks, then receives (i) a therapeutically effective amount of a formulation comprising temozolomide on at least three days during the first week, and (ii) a therapeutically effective amount of a formulation comprising ABDNAZ at least once per week for a duration of at least two weeks. In certain embodiments, the patient after having not received any of temozolomide, radiation therapy, or ABDNAZ for a duration of at least about 2 weeks, then receives (i) a therapeutically effective amount of a formulation comprising temozolomide on at least five days during the first week, and (ii) a therapeutically effective amount of a formulation comprising ABDNAZ at least once per week for a duration of at least 1 month. In certain embodiments, the patient after having not received any of temozolomide, radiation therapy, or ABDNAZ for a duration of at least about 2 weeks, then receives (i) a therapeutically effective amount of a formulation comprising temozolomide on at least five consecutive days during the first week of each 28 day period, and (ii) a therapeutically effective amount of a formulation comprising ABD- NAZ at least once per week for a duration of at least 4 months. In certain embodiments, after receiving temozolomide for a duration of 6 weeks, the patient does not receive any of temozolomide, radiation therapy, or ABDNAZ for a duration of at least about 4 weeks. In certain embodiments, the patient after having not received any of temozolomide, radiation therapy, or ABDNAZ for a duration of at least about 4 weeks, then receives (i) a therapeutically effective amount of a formulation comprising temozolomide on at least three days during the first week, and (ii) a therapeutically effective amount of a formulation comprising ABDNAZ at least once per week for a duration of at least two weeks. In certain embodiments, the patient after having not received any of temozolomide, radiation therapy, or ABDNAZ for a duration of at least about 4 weeks, then receives (i) a therapeutically effective amount of a formulation comprising temozolomide on at least five days during the first week, and (ii) a therapeutically effective amount of a formulation comprising ABDNAZ at least once per week for a duration of at least 1 month. In certain embodiments, the patient after having not received any of temozolomide, radiation therapy, or ABDNAZ for a duration of at least about 4 weeks, then receives (i) a therapeutically effective amount of a formulation comprising temozolomide on at least five consecutive days during the first week of each 28 day period, and (ii) a therapeutically effective amount of a formulation comprising ABDNAZ at least once per week for a duration of at least 4 months.

In certain embodiments, after receiving temozolomide for a duration of 6 weeks, the patient does not receive any of temozolomide, radiation therapy, or ABDNAZ for a duration of about 3 weeks to about 6 weeks.

In certain embodiments, after the duration over which the patient has not received any of temozolomide, radiation therapy, or ABDNAZ, the formulation comprising temozolomide is administered orally to the patient to provide temozolomide in an amount of at least 150 mg/m$^2$. In certain embodiments, after the duration over which the patient has not received any of temozolomide, radiation therapy, or ABDNAZ, the formulation comprising ABDNAZ is administered to the patient by intravenous infusion providing ABDNAZ in an amount of about 5 mg/m$^2$. In certain embodiments, after the duration over which the patient has not received any of temozolomide, radiation therapy, or ABDNAZ, the formulation comprising temozolomide is administered orally to the patient to provide temozolomide in an amount of from about 75 mg/m$^2$ to about 400 mg/m$^2$. In certain embodiments, after the duration over which the patient has not received any of temozolomide, radiation therapy, or ABDNAZ, the formulation comprising temozolomide is administered orally to the patient to provide temozolomide in an amount of from about 150 mg/m$^2$ to about 350 mg/m$^2$. In certain embodiments, after the duration over which the patient has not received any of temozolomide, radiation therapy, or ABDNAZ, the formulation comprising temozolomide is administered orally to the patient to provide temozolomide in an amount of about 150 mg/m$^2$, 200 mg/m$^2$, 250 mg/m$^2$, 300 mg/m$^2$, or 350 mg/m$^2$.

In certain embodiments, after the duration over which the patient has not received any of temozolomide, radiation therapy, or ABDNAZ, the formulation comprising ABDNAZ is administered to the patient by intravenous infusion providing ABDNAZ in an amount of from about 0.1 mg to about 10 mg. In certain embodiments, after the duration over which the patient has not received any of temozolomide, radiation therapy, or ABDNAZ, the formulation comprising ABDNAZ is administered to the patient by intravenous infusion providing ABDNAZ in an amount of from about 0.5 mg to about 4.0 mg. In certain embodiments, after the duration over which the patient has not received any of temozolomide, radiation therapy, or ABDNAZ, the formulation comprising ABDNAZ is administered to the patient by intravenous infusion providing ABDNAZ in an amount of about 0.5 mg, 1.0 mg, 1.5, mg, 2.0 mg, 2.5 mg, 3.0 mg, or 4.0 mg.

Combinations of Embodiments and Illustration of Exemplary More Specific Methods

All combinations of aspects and embodiments described above are contemplated. For example, a therapeutic method is contemplated for treating a glioblastoma by administering to a patient in need thereof (a) for a duration of at least 3 weeks, orally administer one dose of a formulation comprising temozolomide to the patient daily, intravenously administer a formulation comprising ABDNAZ at least once per week, and subject the glioma to radiation therapy at least 3 days each week, and thereafter (b) do not administer any temozolimide, ABDNAZ, or radiation therapy to the patient for at least two weeks, and thereafter (c) orally administer one dose of a formulation comprising temozolimide to the patient at least 3 days each month, and intravenously administer a formulation comprising ABDNAZ at least once per week.

Exemplary more specific illustrations of the contemplated dosing methods for treating a glioma (e.g., a glioblastoma) are provided below in Tables 1, 2, 3, and 4.

TABLE 1

| Step No. | Dosing Schedule |
|---|---|
| 1 | For a duration of at least 3 weeks, orally administer one dose of a formulation comprising temozolimide to the patient daily, intravenously administer a formulation comprising ABDNAZ at least once per week, and subject the glioma to radiation therapy at least 3 days each week. |
| 2 | After completing step 1, do not administer any temozolimide, ABDNAZ, or radiation therapy to the patient for at least two weeks. |
| 3 | After completing step 2, orally administer one dose of a formulation comprising temozolimide to the patient at least 3 days each month, and intravenously administer a formulation comprising ABDNAZ at least once per week. |

TABLE 2

| Step No. | Dosing Schedule |
|---|---|
| 1 | For a duration of at least 3 weeks, orally administer one dose of a formulation comprising temozolimide to the patient daily at a daily dosage of at least 75 mg/m$^2$, intravenously administer a formulation comprising ABDNAZ at least once per week, and subject the glioma to radiation therapy at least 3 days each week. |
| 2 | After completing step 1, do not administer any temozolimide, ABDNAZ, or radiation therapy to the patient for at least two weeks. |
| 3 | After completing step 2, orally administer one dose of a formulation comprising temozolimide to the patient at least 3 days each month, and intravenously administer a formulation comprising ABDNAZ at least once per week. |

TABLE 3

| Step No. | Dosing Schedule |
|---|---|
| 1 | For a duration of at least 6 weeks, orally administer one dose of a formulation comprising temozolimide to the patient daily at a daily dosage of at least 75 mg/m², intravenously administer one dose of a formulation comprising ABDNAZ at least twice once per week wherein each dose of the formulation comprising ABDNAZ provides from about 2.5 mg/m² to about 16.5 mg/m² of ABDNAZ, and subject the glioma to a dose of radiation therapy at least 5 days each week wherein each dose of radiation therapy provides from about 1 Gy to about 3 Gy of radiation. |
| 2 | After completing step 1, do not administer any temozolimide, ABDNAZ, or radiation therapy to the patient for at least four weeks. |
| 3 | After completing step 2, for a duration of at least two months orally administering one dose of a formulation comprising temozolimide to the patient at least 5 days each month wherein each dose of the formulation comprising temozolimide provides from about 150 mg/m² to about 200 mg/m² of temozolimide, and intravenously administer a dose of a formulation comprising ABDNAZ at least once per week where each dose of the formulation comprising ABDNAZ provides at least 5 mg/m² of ABDNAZ. |

TABLE 4

| Step No. | Dosing Schedule |
|---|---|
| 1 | For a duration of at about 6 weeks, orally administer one dose of a formulation comprising temozolimide to the patient daily at a daily dosage of at least 75 mg/m², intravenously administer one dose of a formulation comprising ABDNAZ twice once per week wherein each dose of the formulation comprising ABDNAZ provides from about 2.5 mg/m² to about 16.5 mg/m² of ABDNAZ, and subject the glioma to a dose of radiation therapy 5 days each week wherein each dose of radiation therapy provides about 2 Gy of radiation. |
| 2 | After completing step 1, do not administer any temozolimide, ABDNAZ, or radiation therapy to the patient for about four weeks. |
| 3 | After completing step 2, for a duration of at least two months orally administering one dose of a formulation comprising temozolimide to the patient about 5 days each month wherein each dose of the formulation comprising temozolimide provides from about 150 mg/m² to about 200 mg/m² of temozolimide, and intravenously administer a dose of a formulation comprising ABDNAZ once per week where each dose of the formulation comprising ABDNAZ provides about 5 mg/m² of ABDNAZ. |

A further exemplary more specific dosing method for treating a glioma (e.g., a glioblastoma) is as follows:

Step 1: for a duration of at about 6 weeks, orally administer one dose of a formulation comprising temozolimide to the patient daily at a daily dosage of about 75 mg/m², intravenously administer one dose of a formulation comprising ABDNAZ once per week wherein each dose of the formulation comprising ABDNAZ provides from about 0.5 mg to about 4.0 mg of ABDNAZ, and subject the glioma to a dose of radiation therapy 5 days each week wherein each dose of radiation therapy provides about 2 Gy of radiation. The ABDNAZ is administered within 3 hours prior to administering radiation therapy, and the temozolomide is administered no sooner than 3 hours after administering the ABDNAZ.

Step 2: after completing step 1, do not administer any temozolimide, ABDNAZ, or radiation therapy to the patient for about three to six weeks.

Step 3: after completing step 2, for a duration of at least five months (preferably for six months) orally administer one dose of a formulation comprising temozolimide to the patient about 5 days each month (e.g., days 1-5 of each month) wherein each dose of the formulation comprising temozolimide provides from about 150 mg/m² to about 350 mg/m² of temozolimide, and intravenously administer one dose of a formulation comprising ABDNAZ once per week where each dose of the formulation comprising ABDNAZ provides about from about 0.5 mg to about 4.0 mg of ABDNAZ.

Second Method—Using Irinotecan

Another aspect of the invention provides a method of treating a glioma in a patient. The method comprises the steps of: (a) administering to the patient in need thereof a therapeutically effective amount of a formulation comprising irinotecan, and within about 7 days subjecting the glioma to radiation therapy; and (b) administering to the patient at least one dose of a therapeutically effective amount of a formulation comprising ABDNAZ within about 7 days of administration of a first dose of the irinotecan; to treat the glioma.

Irinotecan is commercially available and marketed in the form of a monohydrochloride trihydrate under the tradename CAMPTOSAR®.

Exemplary Features of the Method

The above method may be further characterized by additional features, such as the dosing schedule and amount of irinotecan, dosing schedule of ABDNAZ, dosing amount for ABDNAZ, features of the radiation therapy, and form of irinotecan.

Dosing Schedule and Amount of Irinotecan

The method can be further characterized according to the dosing schedule and amount of the irinotecan. Accordingly, in certain embodiments, the formulation comprising irinotecan is administered at least once per week for a duration of at least 2 weeks. In certain embodiments, the formulation comprising irinotecan is administered at least once per week for a duration of at least 4 weeks.

In certain embodiments, the patient receives the formulation comprising irinotecan by (i) intravenous infusion once weekly at a single dose of at least about 100 mg/m² of irinotecan, (ii) intravenous infusion once every two weeks at a single dose of at least about 200 mg/m² of irinotecan, or (iii) intravenous infusion once every three weeks at a single dose of at least about 300 mg/m² of irinotecan. In certain embodiments, the patient receives the formulation comprising irinotecan by intravenous infusion once weekly at a single dose of about 125 mg/m² of irinotecan.

Dosing Schedule for ABDNAZ

A formulation comprising ABDNAZ may be administered multiple times, such as multiple times over a defined period of time. Further, coordination of the dosing schedule of the irinotecan and radiation therapy with that of the formulation comprising ABDNAZ is contemplated to provide therapeutic benefits, such as superior efficacy.

In certain embodiments, two doses of a therapeutically effective amount of a formulation comprising ABDNAZ are administered within about 7 days of administration of the first dose of irinotecan. In certain embodiments, for a duration of at least 2 weeks following administration of the first dose of irinotecan, the patient receives two doses each week of a therapeutically effective amount of a formulation comprising ABDNAZ. In certain embodiments, for a duration of at least 4 weeks following administration of the first dose of irinotecan, the patient receives two doses each week of a therapeutically effective amount of a formulation comprising ABDNAZ.

In certain embodiments, for a duration of at least 2 weeks following administration of the first dose of irinotecan, the patient receives one dose each week of a therapeutically effective amount of a formulation comprising ABDNAZ. In certain embodiments, for a duration of at least 4 weeks following administration of the first dose of irinotecan, the patient receives one dose each week of a therapeutically effective amount of a formulation comprising ABDNAZ. In certain embodiments, for a duration of at least 6 weeks following administration of the first dose of irinotecan, the patient receives one dose each week of a therapeutically effective amount of a formulation comprising ABDNAZ. In certain embodiments, for a duration of 6 weeks following administration of the first dose of irinotecan, the patient receives one dose each week of a therapeutically effective amount of a formulation comprising ABDNAZ.

In certain embodiments, the patient receives ABDNAZ within about 6 hours prior to subjecting the glioma to radiation therapy. In certain embodiments, the patient receives ABDNAZ within about 24 hours prior to subjecting the glioma to radiation therapy. In certain embodiments, the patient receives ABDNAZ within about 48 hours prior to subjecting the glioma to radiation therapy.

In certain embodiments, the formulation comprising ABDNAZ is administered so that the ABDNAZ exerts physiological activity during an overlapping time period with one or both of the radiation therapy and irinotecan.

Dose of ABDNAZ Administered

The dose ABDNAZ described herein for use in combination with irinotecan and radiation therapy has been selected in view of the dosing amount and dosing schedule of the irinotecan and radiation therapy. Dosing amounts of ABDNAZ are provided according to the number of milligrams of ABDNAZ to be administered to the patient based on the surface area of the patient as measured in $m^2$.

In certain embodiments, each dose of the formulation comprising ABDNAZ is administered to the patient by intravenous infusion. In certain embodiments, each dose of the formulation comprising ABDNAZ is administered to the patient by intravenous infusion providing ABDNAZ in an amount ranging from about 2 mg/$m^2$ to about 20 mg/$m^2$. In certain embodiments, each dose of the formulation comprising ABDNAZ is administered to the patient by intravenous infusion providing ABDNAZ in an amount ranging from about 2.5 mg/$m^2$ to about 5 mg/$m^2$. In certain embodiments, each dose of the formulation comprising ABDNAZ is administered to the patient by intravenous infusion providing ABDNAZ in an amount ranging from about 5 mg/$m^2$ to about 10 mg/$m^2$. In certain embodiments, each dose of the formulation comprising ABDNAZ is administered to the patient by intravenous infusion providing ABDNAZ in an amount ranging from about 10 mg/$m^2$ to about 16.5 mg/$m^2$. In certain embodiments, each dose of the formulation comprising ABDNAZ is administered to the patient by intravenous infusion providing ABDNAZ in an amount of about 2.5 mg/$m^2$. In certain embodiments, each dose of the formulation comprising ABDNAZ is administered to the patient by intravenous infusion providing ABDNAZ in an amount of about 5 mg/$m^2$. In certain embodiments, each dose of the formulation comprising ABDNAZ is administered to the patient by intravenous infusion providing ABDNAZ in an amount of about 10 mg/$m^2$. In certain embodiments, each dose of the formulation comprising ABDNAZ is administered to the patient by intravenous infusion providing ABDNAZ in an amount of about 16.5 mg/$m^2$.

In certain embodiments, each dose of the formulation comprising ABDNAZ is administered to the patient by intravenous infusion providing ABDNAZ in an amount of from about 0.1 mg to about 20 mg. In certain embodiments, each dose of the formulation comprising ABDNAZ is administered to the patient by intravenous infusion providing ABDNAZ in an amount of from about 0.1 mg to about 10 mg. In certain embodiments, each dose of the formulation comprising ABDNAZ is administered to the patient by intravenous infusion providing ABDNAZ in an amount of from about 0.5 mg to about 4.0 mg. In certain embodiments, each dose of the formulation comprising ABDNAZ is administered to the patient by intravenous infusion providing ABDNAZ in an amount of about 0.5 mg, 1.0 mg, 1.5 mg, 2.0 mg, 2.5 mg, 3.0 mg, 3.5 mg, or 4.0 mg.

Radiation Therapy Features

In certain embodiments, the glioma is subjected to radiation therapy once per day for at least 3 days within a 7 day period following administration of the first dose of irinotecan. In certain embodiments, the glioma is subjected to radiation therapy once per day for at least 5 days within a 7 day period following administration of the first dose of irinotecan. In certain embodiments, for a duration of at least 2 weeks following administration of the first dose of irinotecan, the glioma is subjected to radiation therapy once per day for at least 5 days of each week. In certain embodiments, for a duration of at least 4 weeks following administration of the first dose of irinotecan, the glioma is subjected to radiation therapy once per day for at least 5 days of each week.

In certain embodiments, when radiation therapy is administered to the glioma, the amount of radiation provided to the glioma on the day of administering the radiation therapy is from about 1 Gy to about 3 Gy. In certain embodiments, when radiation therapy is administered to the glioma, the amount of radiation provided to the glioma on the day of administering the radiation therapy is about 2 Gy.

In certain embodiments, the glioma is exposed to from about 50 Gy to about 70 Gy of radiation by the radiation therapy over a period of 6 weeks following administration of the first dose of irinotecan. In certain embodiments, the glioma is exposed to about 60 Gy of radiation by the radiation therapy over a period of 6 weeks following administration of the first dose of irinotecan.

In certain embodiments, the radiation therapy is (i) conventional fractionated external beam radiation or (ii) intensity-modulated radiation therapy. In certain embodiments, the radiation therapy is (i) conventional fractionated external beam radiation.

Various types of radiation therapy are used by those skilled in the art and have been described in the literature. Exemplary types of radiation therapy include, for example, radiation therapy comprising gamma rays, X-rays, electron beams, neutron beams, particulate radiation, proton beams, or the like. The source of the radiation is desirably external to the patient, which involves directing a beam of high-energy radiation to the glioma using a machine external to the patient. Desirably the target site (i.e., site of the glioma) is exposed to the radiation therapy for a short duration of time, such as less than about 3 hours, 2 hours, 1 hour, 30 minutes, 15 minutes, 10 minutes, 5 minutes, or 1 minute for each dose of radiation therapy.

Form of Irinotecan

The method may be further characterized according to the form of irinotecan used, such as a free base or pharmaceutically acceptable salt (such an acid addition salt). In certain embodiments, the formulation comprising irinotecan comprises irinotecan hydrochloride.

Combinations of Embodiments and Illustration of Exemplary More Specific Methods

All combinations of aspects and embodiments described above are contemplated. For example, a therapeutic method is contemplated for treating a glioblastoma by administering to a patient in need thereof (a) for a duration of at least 3 weeks, orally administer one dose of a formulation comprising irinotecan to the patient daily, intravenously administer a formulation comprising ABDNAZ at least once per week, and subject the glioma to radiation therapy at least 3 days each week, and thereafter (b) do not administer any irinotecan, ABDNAZ, or radiation therapy to the patient for at least two weeks, and thereafter (c) orally administer one dose of a formulation comprising irinotecan to the patient at least 3 days each month, and intravenously administer a formulation comprising ABDNAZ at least once per week.

Exemplary more specific illustrations of the contemplated dosing methods for treating a glioma (e.g., a glioblastoma) are provided below in Tables 5, 6, 7, 8, and 9.

TABLE 5

| Step No. | Dosing Schedule |
| --- | --- |
| 1 | For a duration of at least 2 weeks, intravenously administer one dose of a formulation comprising irinotecan to the patient at least once per week wherein each dose provides at least 100 mg/m² of irinotecan, intravenously administer a formulation comprising ABDNAZ at least once per week, and subject the glioma to radiation therapy at least once per week. |
| 2 | After completing step 1, do not administer any irinotecan to the patient for at least one week. |

TABLE 6

| Step No. | Dosing Schedule |
| --- | --- |
| 1 | For a duration of at least 4 weeks, intravenously administer one dose of a formulation comprising irinotecan to the patient at least once per week wherein each dose provides at least 100 mg/m² of irinotecan, intravenously administer a formulation comprising ABDNAZ at least once per week, and subject the glioma to radiation therapy at least twice per week. |
| 2 | After completing step 1, do not administer any irinotecan to the patient for at least two weeks. |

TABLE 7

| Step No. | Dosing Schedule |
| --- | --- |
| 1 | For a duration of at least 2 weeks, intravenously administer one dose of a formulation comprising irinotecan to the patient at least once per week wherein each dose provides at least 125 mg/m² of irinotecan, intravenously administer one dose of a formulation comprising ABDNAZ at least twice once per week wherein each dose of the formulation comprising ABDNAZ provides from about 2.5 mg/m² to about 16.5 mg/m² of ABDNAZ, and subject the glioma to a dose of radiation therapy at least 2 days each week wherein each dose of radiation therapy provides from about 1 Gy to about 3 Gy of radiation. |
| 2 | After completing step 1, do not administer any irinotecan for at least one week. |

TABLE 8

| Step No. | Dosing Schedule |
| --- | --- |
| 1 | For a duration of at least 4 weeks, intravenously administer one dose of a formulation comprising irinotecan to the patient once per week wherein each dose provides at least 125 mg/m² of irinotecan, intravenously administer one dose of a formulation comprising ABDNAZ at least twice once per week wherein each dose of the formulation comprising ABDNAZ provides from about 2.5 mg/m² to about 16.5 mg/m² of ABDNAZ, and subject the glioma to a dose of radiation therapy at least 2 days each week wherein each dose of radiation therapy provides from about 1 Gy to about 3 Gy of radiation. |
| 2 | After completing step 1, do not administer any irinotecan for at least one week. |

TABLE 9

| Step No. | Dosing Schedule |
| --- | --- |
| 1 | For a duration of at least 3 weeks, intravenously administer one dose of a formulation comprising irinotecan to the patient once every three weeks wherein each dose provides at least 350 mg/m² of irinotecan, intravenously administer one dose of a formulation comprising ABDNAZ at least twice once per week wherein each dose of the formulation comprising ABDNAZ provides from about 2.5 mg/m² to about 16.5 mg/m² of ABDNAZ, and subject the glioma to a dose of radiation therapy at least 2 days each week wherein each dose of radiation therapy provides from about 1 Gy to about 3 Gy of radiation. |
| 2 | After completing step 1, do not administer any irinotecan for at least two weeks. |

Third Method—Using Bevacizumab

Another aspect of the invention provides a method of treating a glioma in a patient. The method comprises the steps of: (a) administering to the patient in need thereof a therapeutically effective amount of a formulation comprising bevacizumab, and within about 7 days subjecting the glioma to radiation therapy; and (b) administering to the patient at least one dose of a therapeutically effective amount of a formulation comprising ABDNAZ within about 7 days of administration of a first dose of the bevacizumab; to treat the glioma.

Bevacizumab is a recombinant humanized monoclonal IgG1 antibody that binds to and inhibits the biologic activity of human vascular endothelial growth factor (VEGF) in in vitro and in vivo assay systems. Bevacizumab contains human framework regions and the complementarity-determining regions of a murine antibody that binds to VEGF. Bevacizumab has an approximate molecular weight of 149 kD and can be produced in a mammalian cell (Chinese Hamster Ovary) expression system in a nutrient medium containing the antibiotic gentamicin. Bevacizumab is marketed commercially as AVASTIN®. The formulation of bevacizumab marketed commercially as AVASTIN® is a clear to slightly opalescent, colorless to pale brown, sterile, pH 6.2 solution for intravenous infusion. The formulation is supplied in 100 mg and 400 mg amounts of bevacizumab in preservative-free, single-use vials. The 100 mg product is formulated in 240 mg α,α-trehalose dihydrate, 23.2 mg sodium phosphate (monobasic, monohydrate), 4.8 mg sodium phosphate (dibasic, anhydrous), 1.6 mg polysorbate 20, and Water for Injection, USP. The 400 mg product is formulated in 960 mg α,α-trehalose dihydrate, 92.8 mg sodium phosphate (monobasic, monohydrate), 19.2 mg sodium phosphate (dibasic, a 695 nhydrous), 6.4 mg polysorbate 20, and Water for Injection, USP.

Exemplary Features of the Method

The above method may be further characterized by additional features, such as the dosing schedule and amount of bevacizumab, dosing schedule of ABDNAZ, dosing amount for ABDNAZ, and features of the radiation therapy.

Dosing Schedule and Amount of Bevacizumab

The method can be further characterized according to the dosing schedule and amount of the bevacizumab. Accordingly, in certain embodiments, the formulation comprising bevacizumab is administered once every 2 weeks for a duration of at least 4 weeks. In certain embodiments, the formulation comprising bevacizumab is administered once every 3 weeks for a duration of at least 6 weeks.

In certain embodiments, the patient receives the formulation comprising bevacizumab by (i) intravenous infusion once every 2 weeks at a dose of at least about 5 mg/kg of bevacizumab for a duration of at least 4, 6, 8, 10, or 12 weeks, (ii) intravenous infusion once every 2 weeks at a dose of at least about 10 mg/kg of bevacizumab for a duration of at least 4, 6, 8, 10, or 12 weeks, or (iii) intravenous infusion once every 3 weeks at a dose of at least about 15 mg/kg of bevacizumab for a duration of at least 6, 12, 15, or 18 weeks. In certain embodiments, the patient receives the formulation comprising bevacizumab by intravenous infusion once every 2 weeks at a dose of 5-10 mg/kg of bevacizumab for a duration of at least 4, 6, 8, 10, or 12 weeks.

In certain other embodiments, the patient receives the formulation comprising bevacizumab by (i) intravenous infusion once every 2 weeks at a dose of about 5 mg/kg of bevacizumab for a duration of at least 4, 6, 8, 10, or 12 weeks, (ii) intravenous infusion once every 2 weeks at a dose of about 10 mg/kg of bevacizumab for a duration of at least 4, 6, 8, 10, or 12 weeks, or (iii) intravenous infusion once every 3 weeks at a dose of about 15 mg/kg of bevacizumab for a duration of at least 6, 12, 15, or 18 weeks. In certain embodiments, the patient receives the formulation comprising bevacizumab by intravenous infusion once every 2 weeks at a dose of 5-20 mg/kg of bevacizumab for a duration of at least 4, 6, 8, 10, or 12 weeks.

Dosing Schedule for ABDNAZ

A formulation comprising ABDNAZ may be administered multiple times, such as multiple times over a defined period of time. Further, coordination of the dosing schedule of the bevacizumab and radiation therapy with that of the formulation comprising ABDNAZ is contemplated to provide therapeutic benefits, such as superior efficacy.

In certain embodiments, two doses of a therapeutically effective amount of a formulation comprising ABDNAZ are administered within about 7 days of administration of the first dose of bevacizumab. In certain embodiments, for a duration of at least 2 weeks following administration of the first dose of bevacizumab, the patient receives two doses each week of a therapeutically effective amount of a formulation comprising ABDNAZ. In certain embodiments, for a duration of at least 4 weeks following administration of the first dose of bevacizumab, the patient receives two doses each week of a therapeutically effective amount of a formulation comprising ABDNAZ. In certain embodiments, the patient receives ABDNAZ within about 6 hours prior to subjecting the glioma to radiation therapy. In certain embodiments, the patient receives ABDNAZ within about 24 hours prior to subjecting the glioma to radiation therapy. In certain embodiments, the patient receives ABDNAZ within about 48 hours prior to subjecting the glioma to radiation therapy.

In certain embodiments, the formulation comprising ABDNAZ is administered so that the ABDNAZ exerts physiological activity during an overlapping time period with one or both of the radiation therapy and bevacizumab.

Dose of ABDNAZ Administered

The dose ABDNAZ described herein for use in combination with bevacizumab and radiation therapy has been selected in view of the dosing amount and dosing schedule of the bevacizumab and radiation therapy. Dosing amounts of ABDNAZ are provided according to the number of milligrams of ABDNAZ to be administered to the patient based on the surface area of the patient as measured in $m^2$.

In certain embodiments, each dose of the formulation comprising ABDNAZ is administered to the patient by intravenous infusion. In certain embodiments, each dose of the formulation comprising ABDNAZ is administered to the patient by intravenous infusion providing ABDNAZ in an amount ranging from about 2 $mg/m^2$ to about 20 $mg/m^2$. In certain embodiments, each dose of the formulation comprising ABDNAZ is administered to the patient by intravenous infusion providing ABDNAZ in an amount ranging from about 2.5 $mg/m^2$ to about 5 $mg/m^2$. In certain embodiments, each dose of the formulation comprising ABDNAZ is administered to the patient by intravenous infusion providing ABDNAZ in an amount ranging from about 5 $mg/m^2$ to about 10 $mg/m^2$. In certain embodiments, each dose of the formulation comprising ABDNAZ is administered to the patient by intravenous infusion providing ABDNAZ in an amount ranging from about 10 $mg/m^2$ to about 16.5 $mg/m^2$. In certain embodiments, each dose of the formulation comprising ABDNAZ is administered to the patient by intravenous infusion providing ABDNAZ in an amount of about 2.5 $mg/m^2$. In certain embodiments, each dose of the formulation comprising ABDNAZ is administered to the patient by intravenous infusion providing ABDNAZ in an amount of about 5 $mg/m^2$. In certain embodiments, each dose of the formulation comprising ABDNAZ is administered to the patient by intravenous infusion providing ABDNAZ in an amount of about 10 $mg/m^2$. In certain embodiments, each dose of the formulation comprising ABDNAZ is administered to the patient by intravenous infusion providing ABDNAZ in an amount of about 16.5 mg/m².

Radiation Therapy Features

In certain embodiments, the glioma is subjected to radiation therapy once per day for at least 3 days within a 7 day period following administration of the first dose of bevacizumab. In certain embodiments, the glioma is subjected to radiation therapy once per day for at least 5 days within a 7 day period following administration of the first dose of bevacizumab. In certain embodiments, for a duration of at least 2 weeks following administration of the first dose of bevacizumab, the glioma is subjected to radiation therapy once per day for at least 5 days of each week. In certain embodiments, for a duration of at least 4 weeks following administration of the first dose of bevacizumab, the glioma is subjected to radiation therapy once per day for at least 5 days of each week.

In certain embodiments, when radiation therapy is administered to the glioma, the amount of radiation provided to the glioma on the day of administering the radiation therapy is from about 1 Gy to about 3 Gy. In certain embodiments, when radiation therapy is administered to the glioma, the amount of radiation provided to the glioma on the day of administering the radiation therapy is about 2 Gy.

In certain embodiments, the glioma is exposed to from about 50 Gy to about 70 Gy of radiation by the radiation therapy over a period of 6 weeks following administration of the first dose of bevacizumab. In certain embodiments, the glioma is exposed to about 60 Gy of radiation by the radiation therapy over a period of 6 weeks following administration of the first dose of bevacizumab.

In certain embodiments, the radiation therapy is (i) conventional fractionated external beam radiation or (ii) intensity-modulated radiation therapy. In certain embodiments, the radiation therapy is (i) conventional fractionated external beam radiation.

Various types of radiation therapy are used by those skilled in the art and have been described in the literature. Exemplary types of radiation therapy include, for example, radiation therapy comprising gamma rays, X-rays, electron beams, neutron beams, particulate radiation, proton beams, or the like. The source of the radiation is desirably external to the patient, which involves directing a beam of high-energy radiation to the glioma using a machine external to the patient. Desirably the target site (i.e., site of the glioma) is exposed to the radiation therapy for a short duration of time, such as less than about 3 hours, 2 hours, 1 hour, 30 minutes, 15 minutes, 10 minutes, 5 minutes, or 1 minute for each dose of radiation therapy.

Combinations of Embodiments and Illustration of Exemplary more Specific Methods

All combinations of aspects and embodiments described above are contemplated. For example, a therapeutic method is contemplated for treating a glioblastoma by administering to a patient in need thereof for a duration of at least 3 weeks, orally administer one dose of a formulation comprising bevacizumab to the patient daily, intravenously administer a formulation comprising ABDNAZ at least once per week, and subject the glioma to radiation therapy at least 3 days each week. Exemplary more specific illustrations of the contemplated dosing methods for treating a glioma (e.g., a glioblastoma) using bevacizumab are provided below in Table 10 below describing multiple more specific dosing schedules.

TABLE 10

| Dosing Schedule | Description of Dosing Schedule |
|---|---|
| A | For a duration of at least 4 weeks, intravenously administer one dose of a formulation comprising bevacizumab to the patient once every two weeks wherein each dose provides at least 5 mg/kg of bevacizumab, intravenously administer a formulation comprising ABDNAZ at least once per week, and subject the glioma to radiation therapy at least once per week. |
| B | For a duration of at least 4 weeks, intravenously administer one dose of a formulation comprising bevacizumab to the patient once every two weeks wherein each dose provides at least 5 mg/kg of bevacizumab, intravenously administer a formulation comprising ABDNAZ at least once per week, and subject the glioma to radiation therapy at least twice per week. |
| C | For a duration of at least 4 weeks, intravenously administer one dose of a formulation comprising bevacizumab to the patient once every two weeks wherein each dose provides at least 10 mg/kg of bevacizumab, intravenously administer a formulation comprising ABDNAZ at least once per week, and subject the glioma to radiation therapy at least twice per week. |
| D | For a duration of at least 6 weeks, intravenously administer one dose of a formulation comprising bevacizumab to the patient once every three weeks wherein each dose provides at least 15 mg/kg of bevacizumab, intravenously administer a formulation comprising ABDNAZ at least once per week, and subject the glioma to radiation therapy at least twice per week. |
| E | For a duration of at least 4 weeks, intravenously administer one dose of a formulation comprising bevacizumab to the patient once every two weeks wherein each dose provides at least 5 mg/kg of bevacizumab, intravenously administer a formulation comprising ABDNAZ at least twice per week, and subject the glioma to radiation therapy at least twice per week. |
| F | For a duration of at least 4 weeks, intravenously administer one dose of a formulation comprising bevacizumab to the patient once every two weeks wherein each dose provides at least 10 mg/kg of bevacizumab, intravenously administer a formulation comprising ABDNAZ at least twice per week, and subject the glioma to radiation therapy at least twice per week. |
| G | For a duration of at least 4 weeks, intravenously administer one dose of a formulation comprising bevacizumab to the patient once every two weeks wherein each dose provides at least 5 mg/kg of bevacizumab, intravenously administer a formulation comprising ABDNAZ at least twice per week wherein each dose of the formulation comprising ABDNAZ provides from about 2.5 mg/m² to about 16.5 mg/m² of ABDNAZ, and subject the glioma to radiation therapy at least twice per week wherein each dose of radiation therapy provides from about 1 Gy to about 3 Gy of radiation. |

TABLE 10-continued

| Dosing Schedule | Description of Dosing Schedule |
|---|---|
| H | For a duration of at least 4 weeks, intravenously administer one dose of a formulation comprising bevacizumab to the patient once every two weeks wherein each dose provides at least 10 mg/kg of bevacizumab, intravenously administer a formulation comprising ABDNAZ at least twice per week wherein each dose of the formulation comprising ABDNAZ provides from about 2.5 mg/m² to about 16.5 mg/m² of ABDNAZ, and subject the glioma to radiation therapy at least twice per week wherein each dose of radiation therapy provides from about 1 Gy to about 3 Gy of radiation. |
| I | For a duration of at least 6 weeks, intravenously administer one dose of a formulation comprising bevacizumab to the patient once every three weeks wherein each dose provides at least 15 mg/kg of bevacizumab, intravenously administer a formulation comprising ABDNAZ at least twice per week wherein each dose of the formulation comprising ABDNAZ provides from about 2.5 mg/m² to about 16.5 mg/m² of ABDNAZ, and subject the glioma to radiation therapy at least twice per week wherein each dose of radiation therapy provides from about 1 Gy to about 3 Gy of radiation. |

Further Characterization of the First, Second, and Third Methods

The methods may be further characterized according to, for example, the type of glioma, patients for treatment, effects of the treatment, formulation of ABDNAZ, and form of ABDNAZ.

Type of Glioma

The methods may be further characterized according to the nature of the glioma. In certain embodiments, the glioma is an astrocytoma. In certain embodiments, the glioma is a malignant astrocytoma. In certain embodiments, the glioma is a glioblastoma. In certain embodiments, the glioma is a primary glioblastoma. In certain embodiments, the glioma is a secondary glioblastoma. In certain embodiments, the glioma is a gliosarcoma. In certain embodiments, the glioma is an anaplastic glioma with 1p/19q chromosomes intact. In certain embodiments, the glioma is an anaplastic oligodendroglioma or anaplastic oligoastrocytoma.

Patients for Treatment

The therapeutic method may be further characterized according to the patient to be treated. In certain embodiments, the patient is an adult human. In certain other embodiments, the patient is a pediatric human. In certain embodiments, the patient has previously undergone surgery to remove at least some glioma tissue. In certain embodiments, the patient has previously undergone surgery, to remove at least some glioma tissue, within six weeks prior to receiving the first dose of temozolomide under the methods described herein using ABDNAZ as part of a combination therapy treatment.

Characterization of Treatment Effects

The therapeutic method may be further characterized according to the effect of the treatment, such as (i) a reduction in the size of at least one glioma tumors in the patient, and/or (ii) reduction in the number of glioma tumor in the patient.

Accordingly, in certain embodiments, the therapeutic method is characterized by at least a 20% reduction in the size of at least one glioma tumor in the patient. In certain other embodiments, there is at least a 35% reduction in the size of at least one glioma tumor in the patient. In certain other embodiments, there is at least a 50% reduction in the size of at least one glioma tumor in the patient.

In certain embodiments, there is at least a 20% reduction in the number of glioma tumors in the patient. In certain other embodiments, there is at least a 35% reduction in the number of glioma tumors in the patient. In yet other embodiments, there is at least a 50% reduction in the number of glioma tumors in the patient.

Exemplary Formulations Comprising ABDNAZ

The method may be further characterized according to the formulation comprising ABDNAZ that is administered to the patient. In certain embodiments, the formulation comprises ABDNAZ, dimethylacetamide, water, and a polyethylene glycol. In certain embodiments, the polyethylene glycol has a number-average molecular weight of about 400 g/mol.

Form of ABDNAZ

In certain embodiments, the patient may be administered a pharmaceutically acceptable salt of ABDNAZ.

Methods for Increasing the Amount of Temozolomide, Irinotecan, or Bevacizumab in a Glioma Another aspect of the invention provides a method for increasing the amount of temozolomide, irinotecan, or bevacizumab in a glioma. The method generally involves administering to a patient having a glioma (i) a formulation comprising temozolomide, irinotecan, or bevacizumab and (ii) an effective amount of a formulation comprising ABDNAZ so that the ABDNAZ exerts physiological activity during a time period in which the temozolomide, irinotecan, or bevacizumab is present in the patient, in order to increase the amount of the temozolomide, irinotecan, or bevacizumab in the glioma. The method may be characterized according to the percent increase in the amount of temozolomide, irinotecan, or bevacizumab in the glioma relative to the amount of temozolomide, irinotecan, or bevacizumab in the glioma following an identical administration procedure but absent administering said effective amount of a formulation comprising ABDNAZ.

Accordingly, one aspect of the invention provides a method of increasing the amount of temozolomide in a glioma, where the method comprises administering to a patient having a glioma (i) a formulation comprising temozolomide and (ii) an effective amount of a formulation comprising ABDNAZ so that the ABDNAZ exerts physiological activity during a time period in which the temozolomide is present in the patient, in order to increase the amount of the temozolomide in the glioma.

Another aspect of the invention provides a method of increasing the amount of irinotecan in a glioma, where the method comprises administering to a patient having a glioma (i) a formulation comprising irinotecan and (ii) an effective amount of a formulation comprising ABDNAZ so that the ABDNAZ exerts physiological activity during a time period in which the irinotecan is present in the patient, in order to increase the amount of the irinotecan in the glioma.

Another aspect of the invention provides a method of increasing the amount of bevacizumab in a glioma, where the method comprises administering to a patient having a glioma (i) a formulation comprising bevacizumab and (ii) an effective amount of a formulation comprising ABDNAZ so that the ABDNAZ exerts physiological activity during a time period in which the bevacizumab is present in the patient, in order to increase the amount of the bevacizumab in the glioma.

Each of the foregoing methods may be further characterized according to features described above in connection with the First, Second, and Third Methods. Additionally, the foregoing methods may be further characterized according to the percent increase (e.g., at least a 5%, 10%, 15%, 20%, 25%, 30%, 40%, 50%, 60%, 70%, 80%, 90%, 100%, 200% or 300% increase) in the amount of temozolomide, irinotecan, or bevacizumab in the glioma relative to the amount of temozolomide, irinotecan, or bevacizumab in the glioma following an identical administration procedure but absent administering said effective amount of a formulation comprising ABDNAZ.

In certain embodiments, the formulation comprising ABDNAZ is administered within about 4, 6, 8, 10, 12, 14, 16, 18, 20 or 24 hours of administration of a formulation comprising one of temozolomide, irinotecan, or bevacizumab.

Additional Method—Using Temozolomide

Another aspect of the invention provides a method of treating a glioma in a patient. The method comprises the steps of: (a) administering to the patient in need thereof a therapeutically effective amount of a formulation comprising ABDNAZ, and (b) thereafter administering to the patient in need thereof a therapeutically effective amount of a formulation comprising temozolomide; to treat the glioma. The method may be further characterized by additional features, such as the dosing schedule and amount of temozolomide, dosing schedule of ABDNAZ, dosing amount for ABDNAZ, and/or any rest period/maintenance period, as described above in connection with the First Method.

IV. Pharmaceutical Compositions

The invention provides pharmaceutical compositions comprising an active therapeutic agent and one or more pharmaceutically acceptable carriers (additives) and/or diluents. In certain embodiments, the active therapeutic agent is ABDNAZ, such that the invention provides a pharmaceutical composition comprising ABDNAZ formulated together with one or more pharmaceutically acceptable carriers (additives) and/or diluents. The a pharmaceutical composition may comprise ABDNAZ in a therapeutically effective amount. As described in detail below, the pharmaceutical compositions of the present invention may be specially formulated for administration in liquid form, including those adapted for the following: (1) oral administration, for example, drenches (aqueous or non-aqueous solutions or suspensions); and (2) parenteral administration by, for example, subcutaneous, intramuscular, intravenous or epidural injection as, for example, a sterile solution or suspension, or sustained-release formulation.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

The preparations of the present invention may be given, for example, orally or parenterally. The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

If desired, the effective daily dose of the active compound may be administered as two, three, four, five, six or more sub-doses administered separately at appropriate intervals throughout the day, optionally, in unit dosage forms. Preferred dosing is one administration per day.

The description above describes multiple aspects and embodiments of the invention. The patent application specifically contemplates all combinations and permutations of the aspects and embodiments.

V. Kits for Use in Medical Applications

Another aspect of the invention provides a kit for treating a glioma. The kit comprises: (i) a formulation comprising ABDNAZ, and (ii) instructions for treating a glioma according to procedures described herein, such as (a) administering to the patient in need thereof a therapeutically effective amount of a formulation comprising temozolomide, and within about 2 days thereafter subjecting the glioma to radiation therapy; and (b) administering to the patient at least one dose of a therapeutically effective amount of a formulation comprising ABDNAZ within about 7 days of administration of a first dose of the temozolomide; to treat the glioma. In an alternative embodiment, the kit comprises: (i) a formulation comprising ABDNAZ, and (ii) instructions for treating a glioma that comprise (a) administering to the patient in need thereof a therapeutically effective amount of a formulation comprising irinotecan, and within about 7 days subjecting the glioma to radiation therapy; and (b) administering to the patient at least one dose of a therapeutically effective amount of a formulation comprising ABDNAZ within about 7 days of administration of a first dose of the irinotecan; to treat the glioma.

VI. Definitions

To facilitate an understanding of the present invention, a number of terms and phrases are defined below.

The terms "a" and "an" as used herein mean "one or more" and include the plural unless the context is inappropriate.

As used herein, the term "patient" refers to organisms to be treated by the methods of the present invention. Such organisms are preferably mammals (e.g., murines, simians, equines, bovines, porcines, canines, felines, and the like), and more preferably humans.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route.

As used herein, the term "treating" includes any effect, e.g., lessening, reducing, modulating, ameliorating or eliminating, that results in the improvement of the condition, disease, disorder, and the like, or ameliorating a symptom thereof.

As used herein, the terms "alleviate" and "alleviating" refer to reducing the severity of the condition, such as reducing the severity by, for example, at least 10%, 20%, 30%, 40%, 50%, 60%, 70%, 80%, 90%, or 95%.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see, for example, Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

EXAMPLES

The invention now being generally described, will be more readily understood by reference to the following examples, which are included merely for purposes of illustration of certain aspects and embodiments of the present invention, and are not intended to limit the invention.

Example 1—Treatment of Human Patients Suffering from a Glioblastoma or Malignant Glioma Adult human patients having a gliobastoma or malignant glioma are to be treated using a combination of ABDNAZ, temozolomide, and radiation therapy (RT) according to the treatment protocol described below.

Treatment Protocol

Upfront Therapy

Patients are to receive oral temozolomide 75 mg/m² daily for 6 weeks and undergo conformal or intensity-modulated radiotherapy (60 Gy in 2 Gy fractions) 5 days a week for 6 weeks. Patients are also to receive ABDNAZ by intravenous administration twice weekly for 6 weeks administered at one of four dose levels (2.0 mg/m², 8 mg/m², 17 mg/m², or 29 mg/m²) beginning concurrently with temozolomide and radiotherapy. Cohorts of 3-6 patients will receive escalating doses of ABDNAZ until the maximum feasible dose (MFD) or maximum tolerated dose (MTD) is determined. The MTD is defined as the dose preceding that at which 2 of 3 or 2 of 6 subjects experience dose-limiting toxicity.

Maintenance Therapy

Beginning 28 days after completion of radiotherapy, patients are to receive oral temozolomide [150 mg/m² orally daily for 5 days during cycle 1 (28 days) and 200 mg/m² orally daily for 5 days every 28 days for cycles 2-6] and once weekly ABDNAZ at 2 mg/m² on days 1-28. Treatment will repeat every 4 weeks for up to 12 courses in the absence of disease progression or unacceptable toxicity.

Patient Evaluation Procedure

Patients are to be evaluated by a radiation oncologist and medical oncologist prior to the start of any treatment. Efficacy of the therapy may be evaluated according to procedure described below.

Pre-Treatment Evaluation (within 14±7 Days Prior to First Dose of Study Drug)

Patients may be evaluated using the following criteria prior to treatment with the therapy to assess nature and extent of the gliobastoma or malignant glioma:

GAD-enhanced DCE-MRI

Contrast-enhanced MRI and/or CT

Complete history and general physical exam

Detailed neurological examination

Safety labs: CBC with differential, comprehensive chemistry panel, liver function tests Karnofsky performance status Documentation of primary tumor histology Documentation of steroid and anticonvulsant doses and any other concomitant medications. The newer antiepileptic drugs (levetiracetam, pregabalin, lamotrigine, lacosamide, topiramate) are generally preferred over carbamazepine, phenytoin, phenobarbital, or valproic acid, which stimulate the hepatic cytochrome P450 (CYP) system.

FACT-BR, Barthel Index of ADLs, and neurocognitive function (HVLT-R, COWA, and Trail Making A and B) will be evaluated Evaluation During Radiation Therapy and ABDNAZ Therapy Patients may be evaluated using the following criteria during treatment with the therapy to assess nature and extent of the gliobastoma or malignant glioma:

Clinical visit once per week to include neurological examination, history and physical examination and clinical laboratory testing GAD-enhanced DCE-MRI on days 9±1 day and 41±1 day Collection of concomitant medications at each clinic visit Collection of adverse events (AEs) at each clinic visit Skin within the treatment portal shall be examined once per week during radiation treatment Evaluation after Completion of Radiation Therapy and ABDNAZ Therapy Patients may be evaluated using the following criteria after treatment with the therapy to assess nature and extent of the gliobastoma or malignant glioma:

- Patients are to be evaluated 2 weeks after completion of radiation therapy and ABDNAZ treatment with neurological exam, history and symptom-directed physical examination, and clinical laboratory testing
- During the maintenance phase, patients are to be evaluated on Day 1±2 days of each 4-week cycle. Each evaluation will consist of neurological examination, history and symptom-directed physical examination, ECOG performance status, FACT-BR, Barthel Index of ADLs, and neurocognitive function
- Safety labs every 4 weeks on Day 1±2 days for Cycles 2+(CBC with differential, comprehensive chemistry panel, liver function tests). Radiologic evaluation will occur every 8 weeks as per Standard of Care
- Patients are to be evaluated with contrast-enhanced MRI w/GAD prior to starting Cycle 1 and at least every 2 months (after every 2 cycles) of ABDNAZ/temozolomide as well as neurocognitive testing at 4 months±7 days (1 month=4 weeks or 28 days) after completion of radiation therapy/ABDNAZ
- Collection of concomitant medications at each clinic visit
- Collection of adverse events (AEs) at each clinic visit General Features During Upfront Therapy and Maintenance Therapy described above, temozolomide is to be administered continuously from day 1 of radiotherapy to the last day of radiation at a daily oral dose of 75 mg/m$^2$ for a maximum of 49 days (to allow for treatments interruptions, for example, over holidays). The drug will be administered at night just before bedtime. The dose will be determined using actual body surface area (BSA) as defined by the method of DuBois and DuBois. Capsules of temozolomide are available in 5, 20, 100, 140, 180, and 250 mg. The daily dose is to be rounded to the nearest 5 mg. Patients are to be instructed to swallow the capsules whole, in rapid succession, without chewing them. If vomiting occurs during the course of treatment, no re-dosing of the patient is allowed before the next scheduled dose. The capsules should be taken on an empty stomach, therefore a minimum of 2 hours after eating and with no food consumption for at least 1 hour after temozolomide administration. Water is allowed during the fast period. Administration of the higher dosing regimen during the maintenance phase of the protocol should also be at night. However, prophylaxis with a 5-HT3 antagonist is recommended prior to administration of the first few temozolomide doses and may be administered orally 30 to 60 minutes before temozolomide treatment.

For radiation therapy, 2 Gy of radiation is to be given daily 5 days per week for a total of 60 Gy over 6 weeks. All fields shall be treated during each treatment session. Doses are specified such that at least 95% of the planning treatment volume (PTV) shall receive 100% of the prescribed dose; Dose Volume Histograms (DVHs) may be necessary to make this selection. Radiation therapy will be delivered using standard dose and fractionation as described below:

- Simulation, Immobilization: Patients are to be treated in the supine position. Adequate immobilization and reproducibility of position will be ensured using thermoplastic mask.
- Target: The target volume for both the initial volume and the conedown volume shall be based on CT/MRI. This initial target volume shall include the contrast-enhancing lesion and surrounding edema (if it exists) demonstrated on CT/MRI plus a margin. If no surrounding edema is present, the initial target volume should include the contrast enhancing lesion plus a margin. The initial target volume will be treated to 46 Gy in 23 fractions. After 46 Gy, the tumor volume for the conedown treatment should include the contrast enhancing lesion (without edema) on the CT/MRI scan plus a margin. Isodose distributions for the initial target volume and the conedown target volume are required on all patients, including those treated with parallel opposed fields. The inhomogeneity within the target volume shall be kept to 10%. The minimum dose to the target volume should be kept within 10% of the dose at the center of the volume.
- Dose Limitations: The lens and cervical spine should be shielded from the direct beam at all times. When possible to do without shielding gross tumor, attempts should be made to limit the dose to the optic chiasm to 54 Gy, the retina of at least one eye (but preferably both) to 50 Gy, and the brainstem to 60 Gy. When the optic chiasm must be included in the full dose, then there may be a finite unknown risk of developing blindness.
- Dose Specification: Radiotherapy is to be delivered with a daily fraction size of 2.0 Gy per fraction given 5 days a week for a total of 60 Gy over 6 weeks.
- Technique: Treatment will be delivered with megavoltage machines with a minimum energy of 6 MV photons. All fields will be treated during each treatment session. Treatment plans may include opposed lateral fields, a wedge pair of fields, rotation, or multiple field techniques. Intensity-modulated inverse-planned approaches are permitted. Any of the methods of IMRT (including tomotherapy) may be used, subject to protocol localization and dosimetry constraints. CT-based treatment planning is desirable to assure accuracy in the selection of field arrangements. MRI-fusion for accurate target delineation is recommended.

Example 2—Treatment of Human Patients Suffering from a Glioblastoma or Malignant Glioma Adult human patients having a gliobastoma or malignant glioma are to be treated using a combination of ABDNAZ (by intravenous administration at a dose ranging from 0.5 mg to 4.0 mg), temozolomide, and radiation therapy (RT) according to the treatment protocol described below.

Treatment Protocol

Upfront Therapy

Patients are to receive oral temozolomide 75 mg/m$^2$ daily for 6 weeks and undergo conformal or intensity-modulated radiotherapy (60 Gy in 2 Gy fractions) 5 days a week for 6 weeks. Patients are also to receive ABDNAZ by intravenous administration once weekly for 6 weeks administered at one of four dose levels (0.5 mg, 1.0 mg, 2.0 mg, or 4.0 mg) beginning concurrently with temozolomide and radiotherapy. Cohorts of 3-6 patients will receive escalating doses of ABDNAZ until the maximum feasible dose (MFD) or maximum tolerated dose (MTD) is determined. The MTD is defined as the dose preceding that at which 2 of 3 or 2 of 6 subjects experience dose-limiting toxicity. Administration of temozolomide is no sooner than 4 hours after administration of ABDNAZ. ABDNAZ is preferably administered within three hours prior to administration of radiation therapy.

Maintenance Therapy

Beginning 4-6 weeks after completion of radiotherapy, patients are to receive oral temozolomide [150 mg/m$^2$ orally daily for on days 1-5 during cycle 1 (28 days) and 200 mg/m$^2$ orally daily on days 1-5 during cycles 2-6 (where each cycle is 28 days)] and once weekly ABDNAZ by intravenous administration at a dose ranging from 0.5 mg to 4.0 mg for six months. Administration of temozolomide is no sooner than 4 hours after administration of ABDNAZ.

Patient Evaluation Procedure

Patients are to be evaluated by a neuro-oncologist, radiation oncologist, or medical oncologist prior to the start of any treatment. Efficacy of the therapy may be evaluated according to procedure described below.

Pre-treatment Evaluation (within 14±7 Days Prior to First Dose of Study Drug)

Patients may be evaluated using the following criteria prior to treatment with the therapy to assess nature and extent of the gliobastoma or malignant glioma:
- Contrast-enhanced MRI
- Complete history and general physical exam
- Detailed neurological examination
- Safety labs: CBC with differential, comprehensive chemistry panel with liver function tests
- Karnofsky performance status
- Documentation of primary tumor histology
- Documentation of steroid and anticonvulsant doses and any other concomitant medications. The newer antiepileptic drugs (levetiracetam, pregabalin, lamotrigine, lacosamide, topiramate) are generally preferred over carbamazepine, phenytoin, phenobarbital, or valproic acid, which stimulate the hepatic cytochrome P450 (CYP) system.

Evaluation During Radiation Therapy and ABDNAZ Therapy

Patients may be evaluated using the following criteria during treatment with the therapy to assess nature and extent of the gliobastoma or malignant glioma:
- Clinical visit once per week to include neurological examination, history and physical examination and clinical laboratory testing
- Documentation of concomitant medications at each clinic visit
- Collection of adverse events (AEs) at each clinic visit
- Skin within the treatment portal shall be examined once per week during radiation treatment
- Serum magnesium test during week 4

Evaluation after Completion of Radiation Therapy and ABDNAZ Therapy

Patients may be evaluated using the following criteria after treatment with the therapy to assess nature and extent of the gliobastoma or malignant glioma:
- Patients are to be evaluated 3-5 weeks after completion of radiation therapy and ABDNAZ treatment with neurological exam, history and symptom-directed physical examination, adverse events, concomitant medications, and clinical laboratory testing
- During the maintenance phase, patients are to be evaluated on Day 1±2 days of each 4-week cycle. Each evaluation will consist of neurological examination, history and symptom-directed physical examination, and KPS/ECOG performance status
- Safety labs every 4 weeks on Day 1±2 days for Cycles 2+ (CBC with differential, comprehensive chemistry panel, liver function tests). Radiologic evaluation will occur every 8 weeks as per Standard of Care
- Patients are to be evaluated with contrast-enhanced MRI w/GAD prior to starting Cycle 1 and at least every 2 months (after every 2 cycles) of ABDNAZ/temozolomide as well as neurocognitive testing at 4 months±7 days (1 month=4 weeks or 28 days) after completion of radiation therapy/ABDNAZ
- Collection of concomitant medications at each clinic visit
- Collection of adverse events (AEs) at each clinic visit General Features During Upfront Therapy and Maintenance Therapy described above, temozolomide is to be administered continuously from day 1 of radiotherapy to the last day of radiation at a daily oral dose of 75 mg/m$^2$ for a maximum of 49 days (to allow for treatments interruptions, for example, over holidays). The drug will be administered at night just before bedtime. The dose will be determined using actual body surface area (BSA) as defined by the method of DuBois and DuBois. Capsules of temozolomide are available in 5, 20, 100, 140, 180, and 250 mg. The daily dose is to be rounded to the nearest 5 mg. Patients are to be instructed to swallow the capsules whole, in rapid succession, without chewing them. If vomiting occurs during the course of treatment, no re-dosing of the patient is allowed before the next scheduled dose. The capsules should be taken on an empty stomach, therefore a minimum of 2 hours after eating and with no food consumption for at least 1 hour after temozolomide administration. Water is allowed during the fast period. Administration of the higher dosing regimen during the maintenance phase of the protocol should also be at night. However, prophylaxis with a 5-HT3 antagonist is recommended prior to administration of the first few temozolomide doses and may be administered orally 30 to 60 minutes before temozolomide treatment.

For radiation therapy, 2 Gy of radiation is to be given daily 5 days per week for a total of 60 Gy over 6 weeks. All fields shall be treated during each treatment session. Doses are specified such that at least 95% of the planning treatment volume (PTV) shall receive 100% of the prescribed dose; Dose Volume Histograms (DVHs) may be necessary to make this selection. Radiation therapy will be delivered using standard dose and fractionation as described below:

Simulation, Immobilization: Patients are to be treated in the supine position. Adequate immobilization and reproducibility of position will be ensured using thermoplastic mask.

Target: The target volume for both the initial volume and the conedown volume shall be based on CT/MRI. This initial target volume shall include the contrast-enhancing lesion and surrounding edema (if it exists) demonstrated on CT/MRI plus a margin. If no surrounding edema is present, the initial target volume should include the contrast enhancing lesion plus a margin. The initial target volume will be treated to 46 Gy in 23 fractions. After 46 Gy, the tumor volume for the conedown treatment should include the contrast enhancing lesion (without edema) on the CT/MRI scan plus a margin. Isodose distributions for the initial target volume and the conedown target volume are required on all patients, including those treated with parallel opposed fields. The inhomogeneity within the target volume shall be kept to 10%. The minimum dose to the target volume should be kept within 10% of the dose at the center of the volume.

Dose Limitations: The lens and cervical spine should be shielded from the direct beam at all times. When possible to do without shielding gross tumor, attempts should be made to limit the dose to the optic chiasm to 54 Gy, the retina of at least one eye (but preferably both) to 50 Gy, and the brainstem to 60 Gy. When the optic chiasm must be included in the full dose, then there may be a finite unknown risk of developing blindness.

Dose Specification: Radiotherapy is to be delivered with a daily fraction size of 2.0 Gy per fraction given 5 days a week for a total of 60 Gy over 6 weeks.

Technique: Treatment will be delivered with megavoltage machines with a minimum energy of 6 MV photons. All fields will be treated during each treatment session. Treatment plans may include opposed lateral fields, a wedge pair of fields, rotation, or multiple field techniques. Intensity-modulated inverse-planned approaches are permitted. Any of the methods of IMRT (including tomotherapy) may be used, subject to protocol localization and dosimetry constraints. CT-based treatment planning is desirable to assure accuracy in the selection of field arrangements. MRI-fusion for accurate target delineation is recommended.

Example 3—Administration of Abdnaz and Temozolomide to a GBM14 TMZ-S Patient-Derived Cell Line and a GBM14 TMZ-R Patient-Derived Cell Line Temozolomide-sensitive human GBM14 (GBM14 TMZ-S) patient derived cell line cells were treated with one of the following (i) ABDNAZ, (ii) temozolomide, or (iii) ABDNAZ and temozolomide. In a separate experiment, temozolomide-resistant human GBM14 (GBM14 TMZ-R) patient derived cell line cells were treated with one of the following (i) ABDNAZ, (ii) temozolomide, or (iii) ABDNAZ and temozolomide. Experimental procedures and results are provided below.

Part I—Procedures

In a first experiment, temozolomide-sensitive human GBM14 (GBM14 TMZ-S) patient derived cell line cells were treated with one of the following (i) ABDNAZ at a concentration of 2 μM, (ii) temozolomide at a concentration of 100 μM, or (iii) ABDNAZ (at a concentration of 2 μM) and temozolomide (at a concentration of 100 μM). WST-1 assay was used to assess the effect of treatment on cell viability over the time of three days. The presence of live cells is detected by absorbance at 440 nm in the assay. Data are presented as the mean±3 standard deviations from three separate performances of the experiment.

In a second experiment, temozolomide-resistant human GBM14 (GBM14 TMZ-R) patient derived cell line cells were treated with one of the following (i) ABDNAZ at a concentration of 2 μM, (ii) temozolomide at a concentration of 100 μM, or (iii) ABDNAZ (at a concentration of 2 μM) and temozolomide (at a concentration of 100 μM). The presence of live cells is detected by absorbance at 440 nm in the assay. WST-1 assay was used to assess the effect of treatment on cell viability over the time of three days. Data are presented as the mean±3 standard deviations from three separate performances of the experiment.

Part II—Results

Figure 2:
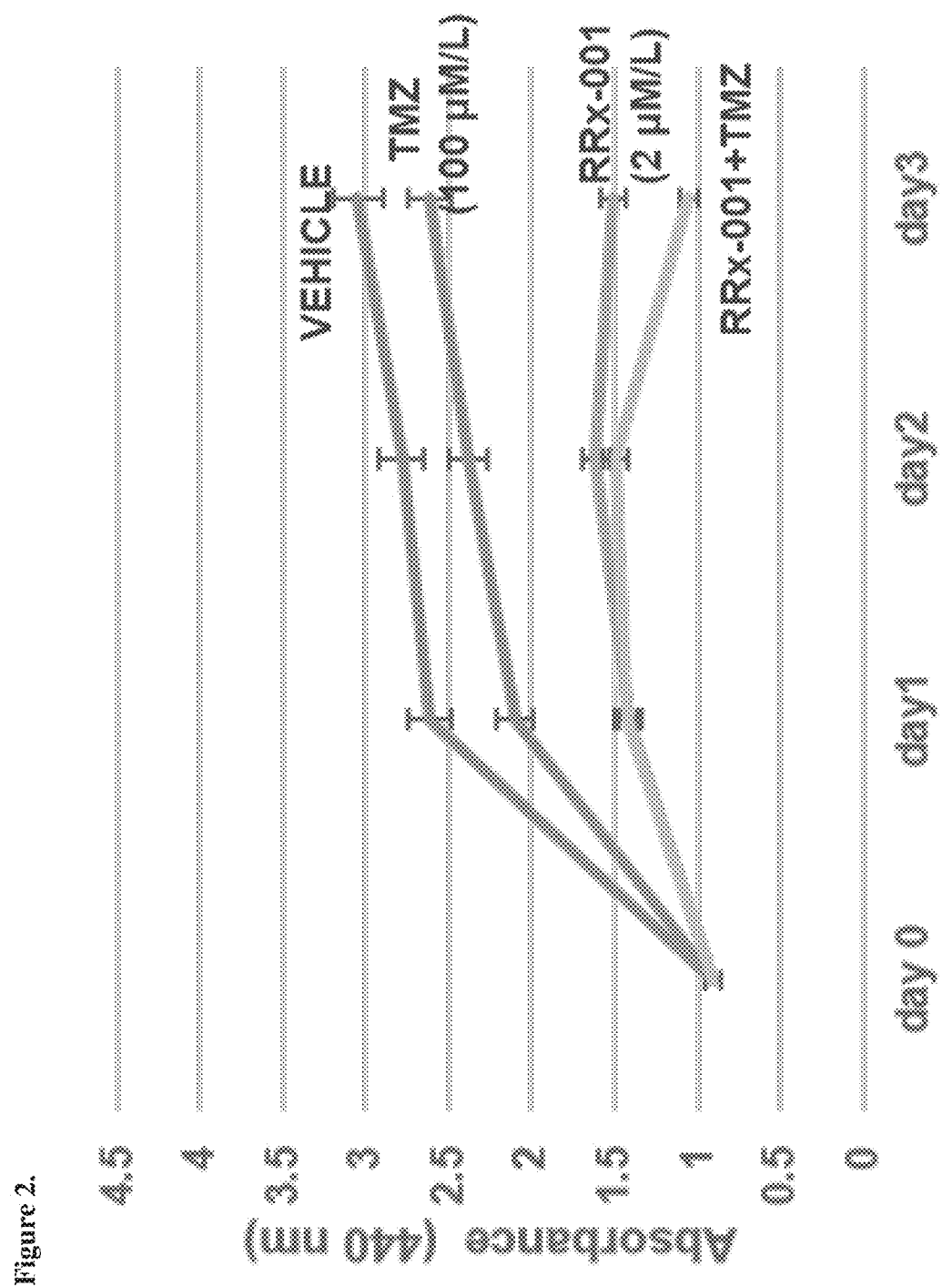
FIG. 2 is a graph showing response observed using a GBM14 TMZ-R patient-derived cell line, as described in Example 3.

Results are presented in FIG. 1 showing response from the GBM14 TMZ-S patient derived cell line and FIG. 2 showing response from the GBM14 TMZ-R patient derived cell line. As indicated by data in FIGS. 1 and 2, administration of ABDNAZ and temozolomide together produced a greater amount of cell death as measured by lack of absorbance at 440 nm.

Example 4—Administration of ABDNAZ and Temozolomide to NSCG Cells In Vitro

Cells from temozolomide-resistant murine EGFRvIII/Arfko neural stem cell-derived glioma (NSCG) cell line were treated with one of the following: (i) ABDNAZ (RRx-001), (ii) temozolomide (TMZ), or (iii) ABDNAZ and temozolomide. Experimental procedures and results are provided below.

Part I—Procedures

Cells from temozolomide-resistant murine EGFRvIII/Arfko neural stem cell-derived glioma (NSCG) cell line were treated with one of the following (i) ABDNAZ at a concentration of 2 μM, (ii) temozolomide at a concentration of 100 μM, or (iii) ABDNAZ (at a concentration of 2 μM) and temozolomide (at a concentration of 100 μM). WST-1 assay was used to assess the effect of treatment on cell viability over the time of five days. The presence of live cells is detected by absorbance at 440 nm in the assay. Data are presented as the mean±3 standard deviations from three separate performances of the assay.

Part II—Results

Figure 3:
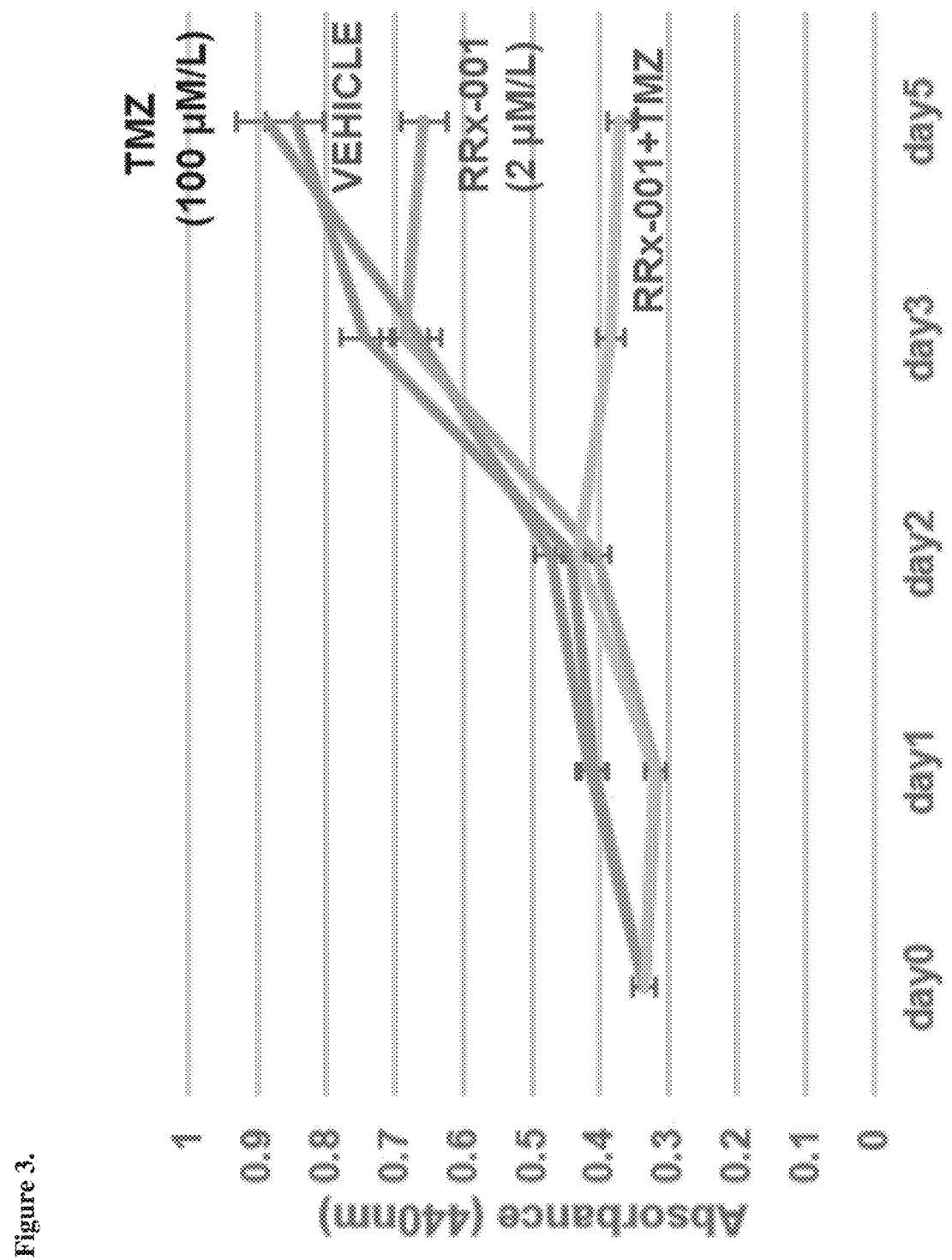
FIG. 3 is a graph showing response observed using cells from temozolomide-resistant murine EGFRvIII/Arfko neural stem cell-derived glioma (NSCG) cell line, as described in Example 4.

Results are presented in FIG. 3, where the data indicate that administration of ABDNAZ and temozolomide together produced a greater amount of cell death as measured by lack of absorbance at 440 nm. Data are presented as the mean±3 standard deviations from three separate performances of the assay.

Example 5—Administration of ABDNAZ and Temozolomide to Mice Implanted with NSCG Tumors Mice implanted with temozolomide-resistant EGFRvIII/Arfko GBM (NSCG) cells were treated with (i) ABDNAZ (RRx-001, 10 mg/kg, intraperitoneal injection), (ii) temozolomide (TMZ)(40 mg/kg, oral gavage), or (iii) ABDNAZ (10 mg/kg, intraperitoneal injection) and temozolomide (40 mg/kg, oral gavage). Experimental procedures and results are provided below.

Part I—Procedures

NSCG tumors were intracranially injected into FVBN mice. Mice to be treated were treated with one of the following (i) ABDNAZ (10 mg/kg, intraperitoneal injection), (ii) temozolomide (40 mg/kg, oral gavage), or (iii) ABDNAZ (10 mg/kg, intraperitoneal injection) and temozolomide (40 mg/kg, oral gavage). In a first experiment, treatment (i.e., administration of ABDNAZ (RRx-001), temozolomide (TMZ), or both ABDNAZ and temozolomide) was started five days after intracranial injection of NSCG cells. The control population of mice contained ten mice, the group receiving only ABDNAZ had twelve mice, the group receiving only temozolomide had twelve mice, and the group receiving both ABDNAZ and temozolomide had sixteen mice. Mouse survival was monitored over time.

In a second experiment, treatment (i.e., administration of ABDNAZ (RRx-001), temozolomide (TMZ), or both ABDNAZ and temozolomide) was started ten days after intracranial injection of NSCG cells. The control population of mice contained three mice, the group receiving only ABDNAZ had five mice, the group receiving only temozolomide had four mice, and the group receiving both ABDNAZ and temozolomide had six mice. Mouse survival was monitored over time.

Part II—Results

Figure 4:
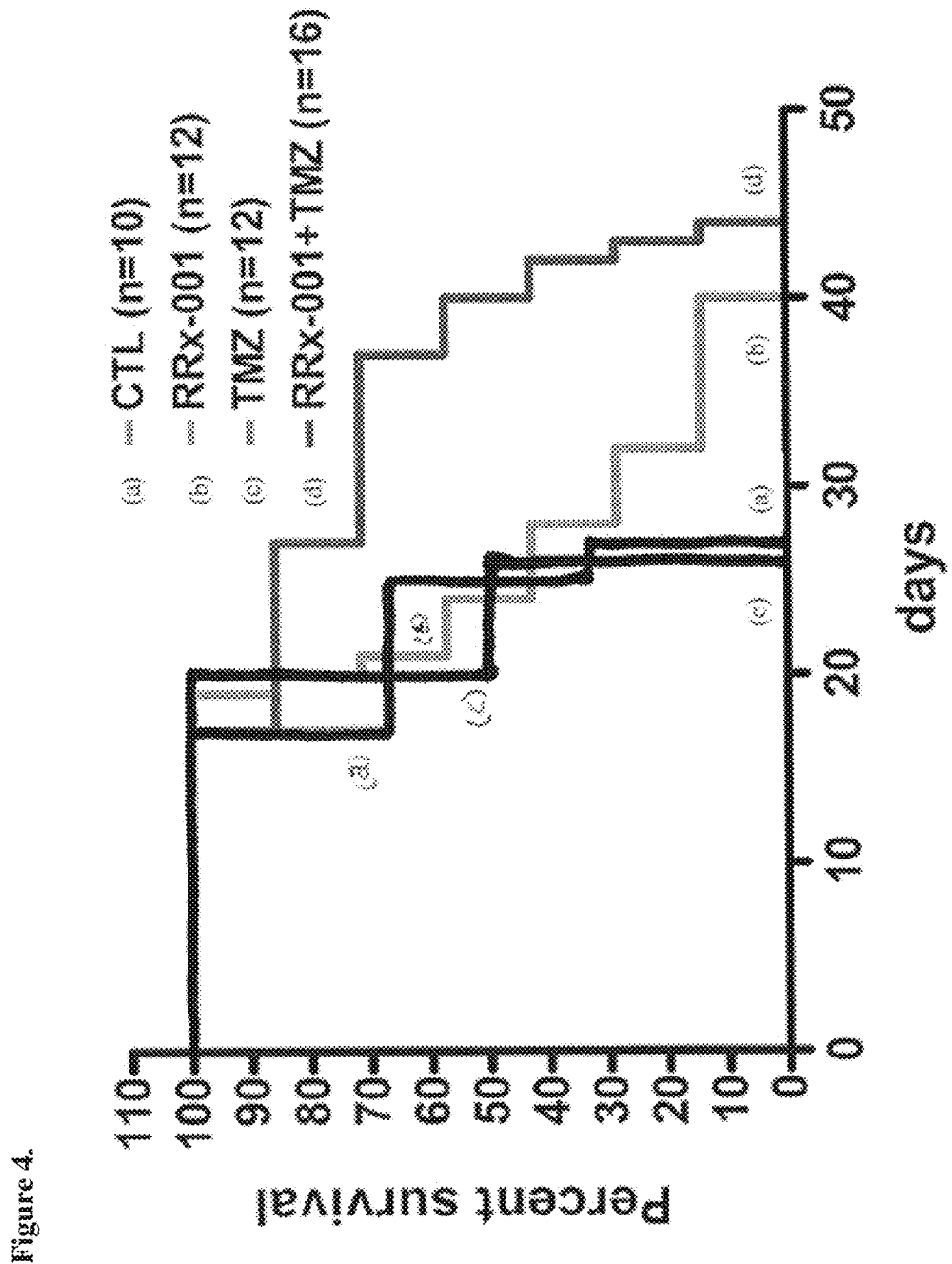
FIG. 4 is a graph showing percent survival of subjects over time, in the experiment in which treatment (i.e., administration of ABDNAZ (RRx-001), temozolomide (TMZ), or both ABDNAZ and temozolomide) was started five days after intracranial injection of NSCG cells, as described in Example 5.

Results are presented in FIGS. 4 and 5 and Tables 1 and 2 below. FIG. 4 is a graph showing percent survival of subjects over time, in the experiment in which treatment (i.e., administration of ABDNAZ (RRx-001), temozolomide (TMZ), or both ABDNAZ and temozolomide) was started five days after intracranial injection of NSCG cells. The abbreviation "CTL" in FIG. 4 refers to control subjects. Table 1 shows median survival time (in days) observed in the experiment in which treatment (i.e., administration of ABDNAZ (RRx-001), temozolomide (TMZ), or both ABDNAZ and temozolomide) was started five days after intracranial injection of NSCG cells.

Figure 5:
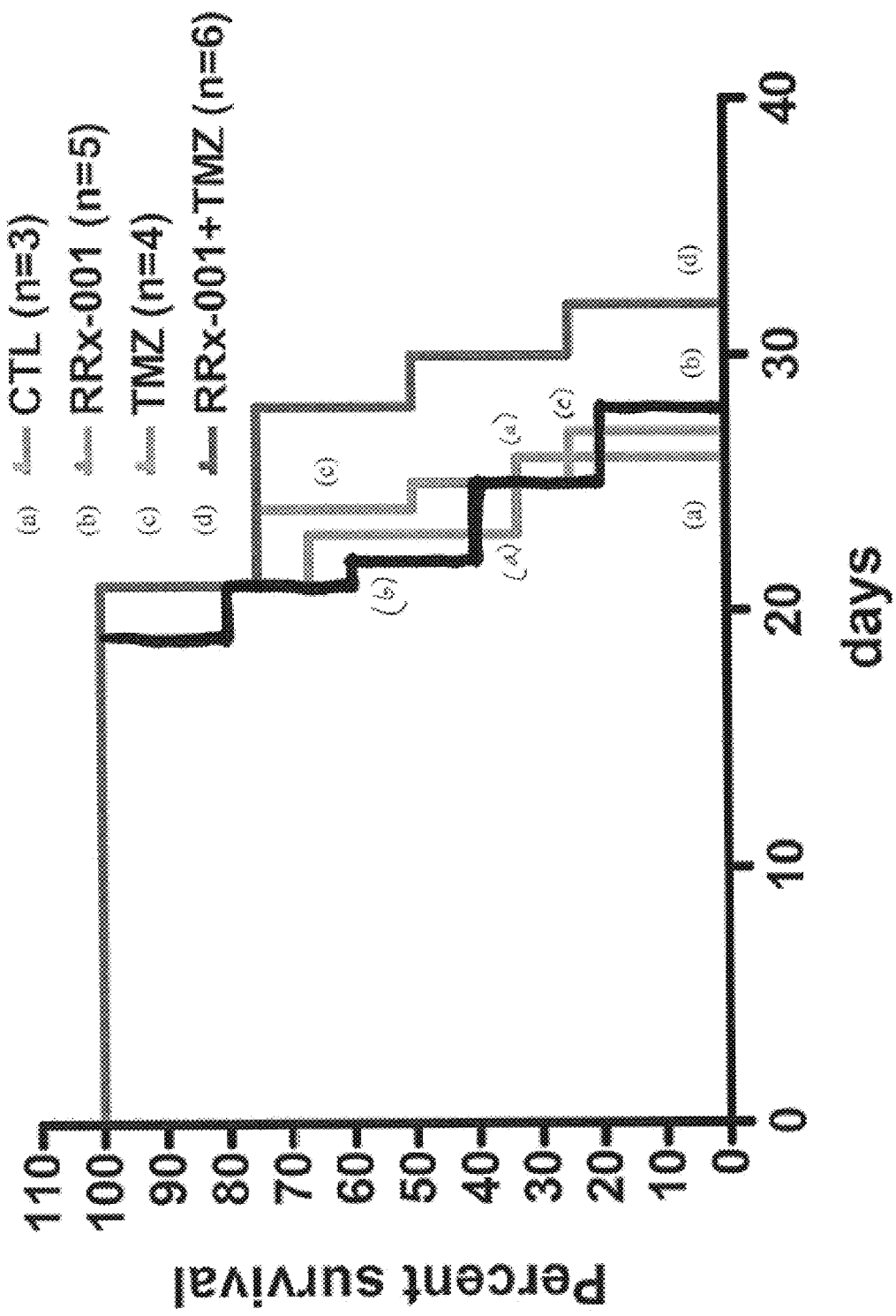
FIG. 5 is a graph showing percent survival of subjects over time, in the experiment in which treatment (i.e., administration of ABDNAZ (RRx-001), temozolomide (TMZ), or both ABDNAZ and temozolomide) was started ten days after intracranial injection of NSCG cells, as described in Example 5.

FIG. 5 is a graph showing percent survival of subjects over time, in the experiment in which treatment (i.e., administration of ABDNAZ (RRx-001), temozolomide (TMZ), or both ABDNAZ and temozolomide) was started ten days after intracranial injection of NSCG cells. The abbreviation "CTL" in FIG. 5 refers to control subjects. Table 2 shows median survival time (in days) observed in the experiment in which treatment (i.e., administration of ABDNAZ (RRx-001), temozolomide (TMZ), or both ABDNAZ and temozolomide) was started ten days after intracranial injection of NSCG cells.

TABLE 1

| | Subjects | | | |
|---|---|---|---|---|
| | Control | Population Receiving Only TMZ | Population Receiving Only ABDNAZ | Population Receiving Both ABDNAZ & TMZ |
| Median Survival Time (days) | 22.2 | 22.3 (ns) | 25.3 (p = 0.072) | 30.4 (p = 0.003) |

TABLE 2

| | Subjects | | | |
|---|---|---|---|---|
| | Control | Population Receiving Only TMZ | Population Receiving Only ABDNAZ | Population Receiving Both ABDNAZ & TMZ |
| Median Survival Time (days) | 22.1 | 22.3 (ns) | 22.5 (ns) | 27.2 (p = 0.174) |

Figure 6:
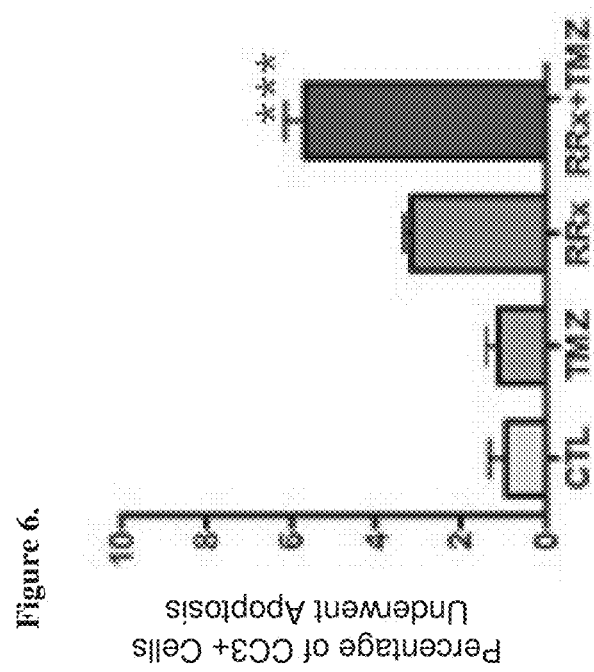
FIG. 6 is a graph showing the amount of CC3+ cell apoptosis detected in the assay, as described in Example 6.

Example 6—Administration of ABDNAZ and Temozolomide to Mice Implanted with NSCG Tumors Mice implanted with TMZ-resistant EGFRvIII/Arfko GBM tumors (NSCG tumors) were treated with ABDNAZ (RRx-001), temozolomide (TMZ), or both ABDNAZ and temozolomide. Experimental procedures and results are provided below.
Part I—Procedures
NSCG tumors were orthotopically implanted in FVBN mice. Then, the mice were treated with one of the following (i) ABDNAZ (10 mg/kg, intraperitoneal injection), (ii) temozolomide (40 mg/kg, oral gavage), or (iii) ABDNAZ (10 mg/kg, intraperitoneal injection) and temozolomide (40 mg/kg, oral gavage). Percent apoptosis of CC3+ cells was evaluated.
Part II—Results
The amount of CC3+ cell apoptosis detected in the assay is shown in FIG. 6. As indicated by data in FIG. 6, administration of ABDNAZ and temozolomide together produced the highest percentage of CC3+ cell apoptosis. The abbreviation "CTL" refers to control mice; the symbol *** refers to p<0.001.

Figure 7:
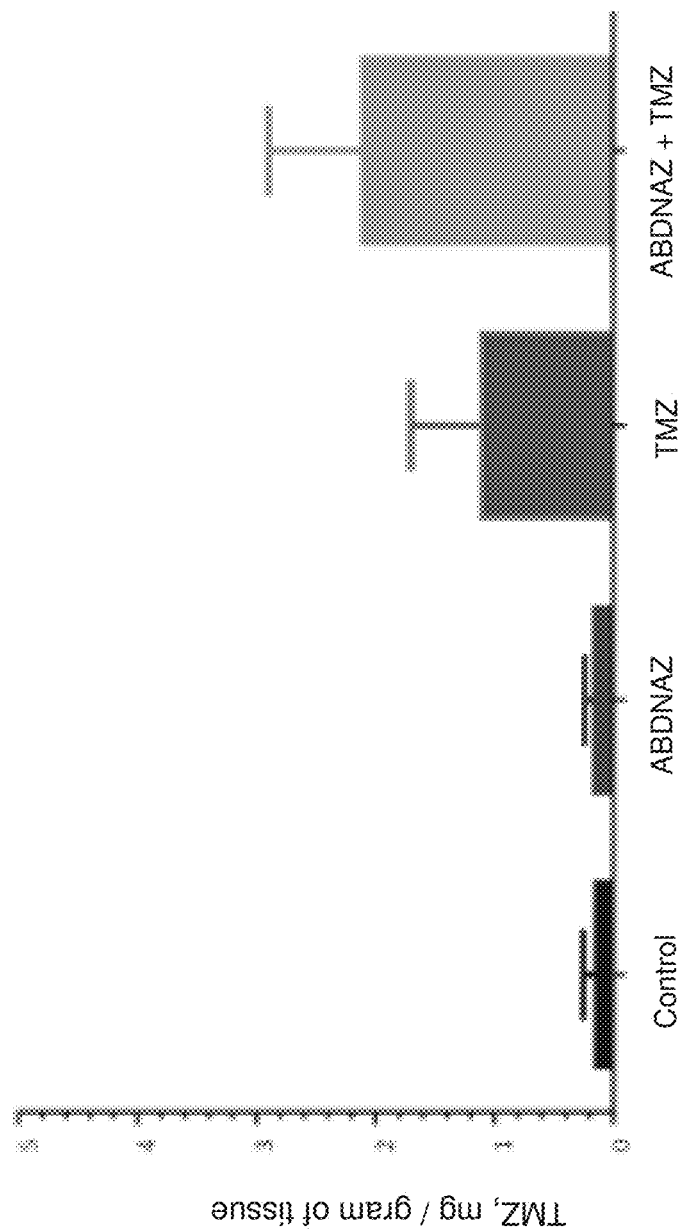
FIG. 7 is a graph showing the amount of TMZ (mg) detected per gram of tissue analyzed, as described in Example 7.

Example 7—Administration of ABDNAZ and Temozolomide to Mice Implanted with Brain Tumors Mice implanted with brain tumors were treated with ABDNAZ, temozolomide (TMZ), or both ABDNAZ and temozolomide. Experimental procedures and results are provided below.
Part I—Procedures
Brain tumors were orthotopically implanted in the brain of mice. Then, the mice were treated with one of the following (i) ABDNAZ, (ii) temozolomide, or (iii) ABDNAZ followed by administration of temozolomide 4 hours later. ABDNAZ (10 mg/kg) was administered via tail vein 4 hours before any temozolomide (20 mg/kg) via tail vein once weekly for 4 weeks. Twenty-four hours after temozolomide administration, tumor-bearing mice were euthanized and brain tumor tissue was collected and dissected. Temozolomide levels in tumor tissues were measured.
Part II—Results
The concentration of temozolomide (TMZ) detected in brain tumor tissue of the mice is shown in FIG. 7. As indicated by data in FIG. 7, administration of ABDNAZ prior to administration of temozolomide resulted in a greater concentration of temozolomide in the brain tumor tissue.

Figure 8:
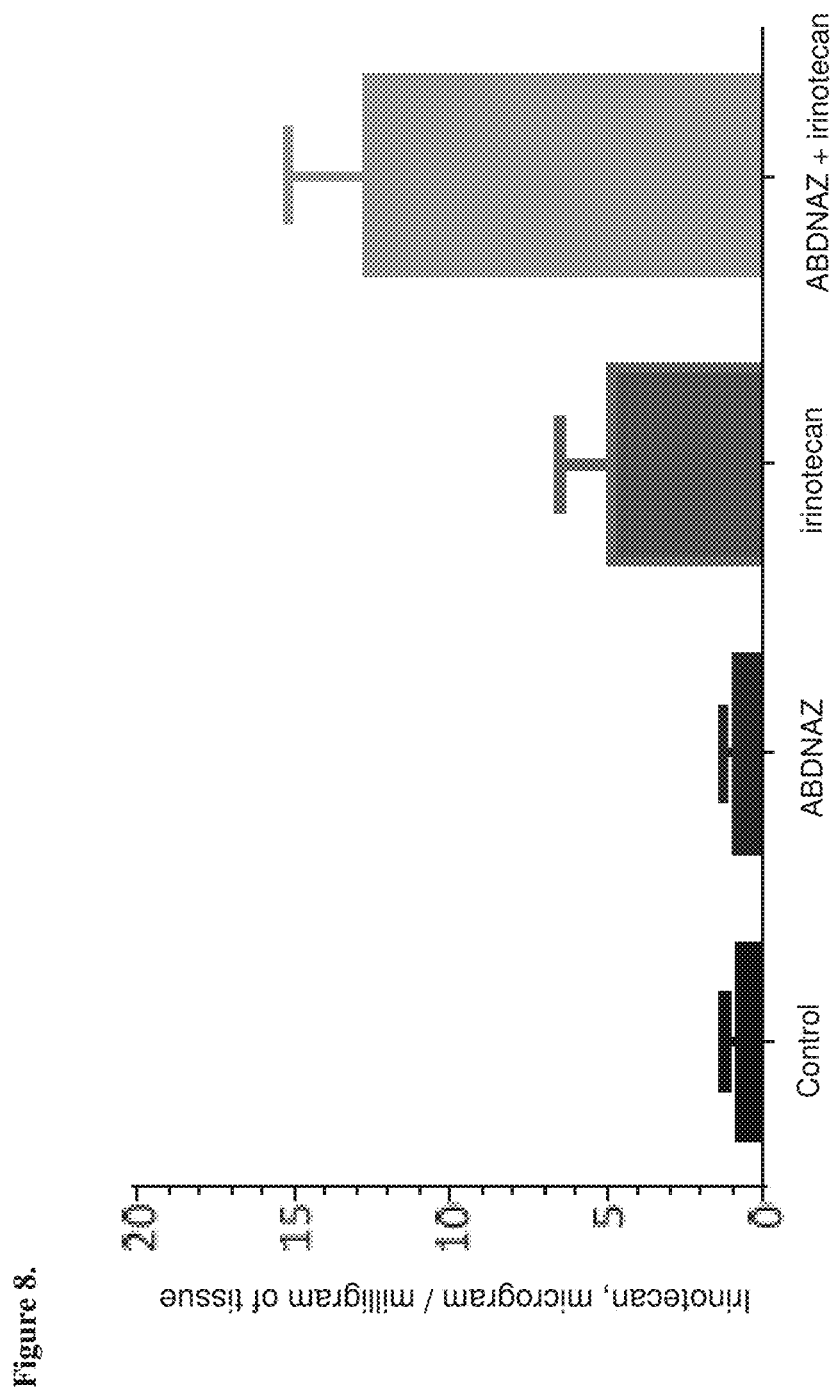
FIG. 8 is a graph showing the amount of irinotecan (μg) detected per milligram of tissue analyzed, as described in Example 8.

Example 8—Administration of ABDNAZ and Irinotecan to Mice Implanted with Human Glioblastoma GBM43 Brain Tumors Mice implanted with human glioblastoma GBM43 brain tumors were treated with ABDNAZ, irinotecan, or both ABDNAZ and irinotecan. Experimental procedures and results are provided below.
Part I—Procedures
Human glioblastoma GBM43 tumors were orthotopically implanted in the brain of immunocompromised mice. Then, the mice were treated with one of the following (i) ABDNAZ, (ii) irinotecan, or (iii) ABDNAZ followed by administration of irinotecan 4 hours later. Twenty-four hours after irinotecan administration, tumor-bearing mice were euthanized and brain tumor tissue was collected and dissected. Irinotecan levels in tumor tissues were measured.
Part II—Results
The concentration of irinotecan detected in brain tumor tissue of the mice is shown in FIG. 8. As indicated by data in FIG. 8, administration of ABDNAZ prior to administration of irinotecan resulted in a greater concentration of irinotecan in the brain tumor tissue.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

The invention claimed is:

1. A method of treating a glioma in a human, comprising the steps of:
   (a) administering to the patient in need thereof a therapeutically effective amount of a formulation comprising temozolomide, and within about 2 days thereafter subjecting the glioma to radiation therapy; and
   (b) administering to the patient at least one dose of a therapeutically effective amount of a formulation comprising ABDNAZ within about 7 days of administration of a first dose of the temozolomide; to treat the glioma.

2. The method of claim 1, wherein the formulation comprising temozolomide is administered daily for at least 2 weeks.

3. A method of treating a glioma in a human, comprising the steps of:
   (a) administering to the patient in need thereof a therapeutically effective amount of a formulation comprising irinotecan, and within about 7 days subjecting the glioma to radiation therapy; and
   (b) administering to the patient at least one dose of a therapeutically effective amount of a formulation comprising ABDNAZ within about 7 days of administration of a first dose of the irinotecan; to treat the glioma.

4. The method of claim 3, wherein the formulation comprising irinotecan is administered at least once per week for a duration of at least 2 weeks.

5. The method of claim 1, wherein the human is an adult human.

6. The method of claim 1, wherein the human is a pediatric human.

7. The method of claim 1, wherein there is at least a 20% reduction in the size of at least one glioma tumor in the human.

8. The method of claim 1, wherein there is at least a 20% reduction in the number of glioma tumors in the human.

9. The method of claim 3, wherein the human is an adult human.

10. The method of claim 3, wherein the human is a pediatric human.

11. The method of claim 3, wherein there is at least 20% reduction in the size of at least one glioma tumor in the human.

12. The method of claim 3, wherein there is at least a 20% reduction in the number of glioma tumors in the human.

* * * * *